US010206618B2

(12) United States Patent
Vuong et al.

(10) Patent No.: US 10,206,618 B2
(45) Date of Patent: Feb. 19, 2019

(54) OPTIMIZED VISIBILITY FOR SLEEP SESSIONS OVER TIME

(71) Applicant: Microsoft Technology Licensing, LLC, Redmond, WA (US)

(72) Inventors: Victor Vuong, Kirkland, WA (US); Sarthak Datt, Bellevue, WA (US); Katherine W. Osborne, Kirkland, WA (US); Maria Isabel Ancona, Seattle, WA (US); Nazia Zaman, Kirkland, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 724 days.

(21) Appl. No.: 14/624,534

(22) Filed: Feb. 17, 2015

(65) Prior Publication Data

US 2016/0239609 A1    Aug. 18, 2016

(51) Int. Cl.
*A61B 5/00*    (2006.01)
*G16H 40/63*   (2018.01)
(Continued)

(52) U.S. Cl.
CPC .......... *A61B 5/4812* (2013.01); *A61B 5/4806* (2013.01); *A61B 5/4821* (2013.01);
(Continued)

(58) Field of Classification Search
CPC ....... G06Q 50/22–50/24; A61B 5/4806; A61B 5/4809; A61B 5/4812; A61B 5/4815;
(Continued)

(56) References Cited

U.S. PATENT DOCUMENTS 6,579,233 B2    6/2003   Hursh
7,693,773 B2    4/2010   Hockley et al.
(Continued)

FOREIGN PATENT DOCUMENTS

JP    5361018 B2 * 12/2013  ........... A61B 5/0002

OTHER PUBLICATIONS

Dalgleish, Debra, "Leno and Conan Excel Gantt Chart", http://blog.contextures.com/archives/2010/01/13/lenoandconanexcelgantt-tchart/, Published on Jan. 13, 2010.*
(Continued)

*Primary Examiner* — Elaine Gort
*Assistant Examiner* — Eric M. Williams
(74) *Attorney, Agent, or Firm* — Mark K. Young; Mayer & Williams PC

(57) ABSTRACT

A sleep application running on a computing platform such as a server utilizes sleep data from a remote system that monitors a user's sleep behaviors and transforms the data to populate graphs of sleep sessions over various calendar periods (e.g., by week, by month) and render them on a user interface (UI) that is exposed to remote devices such as personal computers (PCs), tablets, multimedia consoles, and smartphones over a network. The sleep sessions are optimized for visibility on the remote devices by dynamically adjusting the range of the time axis of a graph so that a maximum number of sleep sessions over a calendar period may be graphed continuously over the range without breaks (which can impair visibility and reduce comprehension).

20 Claims, 17 Drawing Sheets

(51) Int. Cl.
  *G16H 15/00* (2018.01)
  *G16H 10/65* (2018.01)
  *G06F 19/00* (2018.01)
  *G16H 10/60* (2018.01)

(52) U.S. Cl.
  CPC .......... *G06F 19/00* (2013.01); *G06F 19/3418* (2013.01); *G16H 10/65* (2018.01); *G16H 15/00* (2018.01); *G16H 40/63* (2018.01); *G16H 10/60* (2018.01)

(58) Field of Classification Search
  CPC ...... A61B 5/4821; G16H 40/63; G16H 15/00; G16H 10/65; G16H 19/00; G16H 10/60; G06F 19/3418
  See application file for complete search history.

(56) References Cited

U.S. PATENT DOCUMENTS

| | | | |
|---|---|---|---|
| 8,002,553 B2 | 8/2011 | Hatlestad et al. | |
| 8,245,153 B2 * | 8/2012 | Sharp | G06Q 10/06 715/786 |
| 8,617,068 B2 * | 12/2013 | Doherty | A61B 5/0476 600/26 |
| 8,836,726 B1 | 9/2014 | Schickler | |
| 10,049,474 B2 * | 8/2018 | Germain | G01V 1/003 |
| 2002/0161853 A1 | 10/2002 | Burak et al. | |
| 2008/0157956 A1 * | 7/2008 | Radivojevic | A61B 5/11 340/531 |
| 2008/0177158 A1 * | 7/2008 | Teller | A61B 5/411 600/301 |
| 2010/0049008 A1 | 2/2010 | Doherty et al. | |
| 2011/0152704 A1 | 6/2011 | Yoshizawa | |
| 2012/0092171 A1 | 4/2012 | Hwang et al. | |
| 2013/0002435 A1 * | 1/2013 | Utter, II | A61B 5/0022 340/575 |
| 2013/0018284 A1 | 1/2013 | Kahn et al. | |
| 2013/0261404 A1 | 10/2013 | Sato et al. | |
| 2013/0310712 A1 * | 11/2013 | Kanemitsu | A61B 5/11 600/595 |
| 2014/0163343 A1 * | 6/2014 | Heneghan | A61B 5/0507 600/324 |
| 2015/0046856 A1 * | 2/2015 | Rucker | G06F 3/04883 715/765 |
| 2016/0192218 A1 * | 6/2016 | Peters | A61B 5/4815 370/252 |

OTHER PUBLICATIONS

"International Search Report and Written Opinion Issued in PCT Application No. PCT/US2016/016478", dated May 12, 2016, (14 Pages total).

Glance, David, "Dream Appzzz: can the iPhone help you sleep?", Published on: Mar. 5, 2012, Available at: http://theconversation.com/dream-appzzz-can-the-iphone-help-you-sleep-5688 (5 pages total).

"Sleep Cycle App Review: 997 Nights and Counting", Published on: Aug. 21, 2014, Available at: http://mymorningroutine.com/sleep-cycle-review/ (6 pages total).

Stephen, Duncan, "Sleeping Patterns: Update After Nine Months", Published on: Oct. 1, 2008, Available at: http://doctorvee.co.uk/2008/10/01/sleeping-patterns-update-after-nine-months/ (4 pages total).

Rettner, Rachael, "Runtastic Orbit: Fitness Tracker Review", Published on: Aug. 19, 2014, Available at: http://www.livescience.com/47442-runtastic-orbit-fitness-tracker-review.html (9 pages total).

"Do Grains and Sugar Affect Sleep?—My Experiment", Published on: Aug. 30, 2008, Available at: http://www.sleepwarrior.com/do-grains-and-sugar-affect-sleep-my-experiment (10 pages total).

"Continually Updated Data on Lilah", Published on: Nov. 2, 2007, Available at: http://web.gps.caltech.edu/~mbrown/lilah/sleep/Sleep_Data.html (31 pages total).

* cited by examiner

OPTIMIZED VISIBILITY FOR SLEEP SESSIONS OVER TIME

BACKGROUND

Users of computing devices are often interested in using applications that provide engaging health and fitness experiences and gain actionable insights based on data gathered and expressed by the applications.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

A sleep application running on a computing platform such as a server utilizes sleep data from a remote system that monitors a user's sleep behaviors and transforms the data to populate graphs of sleep sessions over various calendar periods (e.g., by week, by month) and render them on a user interface (UI) that is exposed to remote devices such as personal computers (PCs), tablets, multimedia consoles, and smartphones over a network. The sleep sessions are optimized for visibility on the remote devices by dynamically adjusting the range of the time axis of a graph so that a maximum number of sleep sessions over a calendar period may be graphed continuously over the range without breaks (which can impair visibility and reduce comprehension). The sleep application can also apply processes to transform sleep session data to optimize visibility on the UI when sleep is distributed during the course of a day, such as when the user naps, and also generate the graphs so that the greatest amount of data is centered in the graph. Sleep sessions that span day boundaries can also be wrapped, in some cases, while maintaining optimized visibility using the dynamically adjusted range on the time axis.

In an illustrative non-limiting example, the sleep application may utilize a graphing process to determine the time range expressed in a graph by running through the 24 hours in a given day by placing each hour (or some other time increment) on the minimum/start point of the time axis and then determining if starting the graph at that hour produces the most number of continuous sleep sessions without breaks in the expressed data. The process is iterated until a beginning point is determined for the range that provides the optimized visibility for the sleep sessions. The maximum value (i.e., the end point of the range) on the time axis is determined based on the end time of the sleep sessions over the calendar period.

By transforming the collected sleep data to optimize visibility, the sleep application enables increased user efficiency in comprehending the sleep session data and improves user interaction performance with the device. The continuous representation of sleep sessions enables users to understand bed times and wake up times at a glance and readily gain an appreciation of the length and quality of sleep sessions over a given calendar period. The optimized visibility of the transformed sleep data enables users to gain a maximum of information with a limited amount of interaction with the device and reduces the need to take additional steps to synthesize the information themselves, which can lead to errors. It can also reduce the need for the user to retrieve additional screens of information, which lowers the likelihood of unintentional inputs to the device that can cause additional resource consumption and user frustration. The visibility optimization and centering of a maximum amount of data on the UI also enables less space on the device screen to be utilized when providing the present sleep application features and functionalities.

In addition, the sleep application enables the remote devices to more efficiently utilize available computing resources including network bandwidth, processing cycles, memory, and battery life in some cases. For example, by maximizing the amount of data rendered on the UI so that the sleep sessions are shown in a continuous, non-broken manner in the graphs, the user can reduce the number of screens of information that need to be downloaded over the network, and then processed and rendered on the device in some cases and/or reduce the processing on the device that might otherwise be needed to convey the sleep session information to the user.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure. It may be appreciated that the above-described subject matter may be implemented as a computer-controlled apparatus, a computer process, a computing system, or as an article of manufacture such as one or more computer-readable storage media. These and various other features may be apparent from a reading of the following Detailed Description and a review of the associated drawings.

Figure 1:
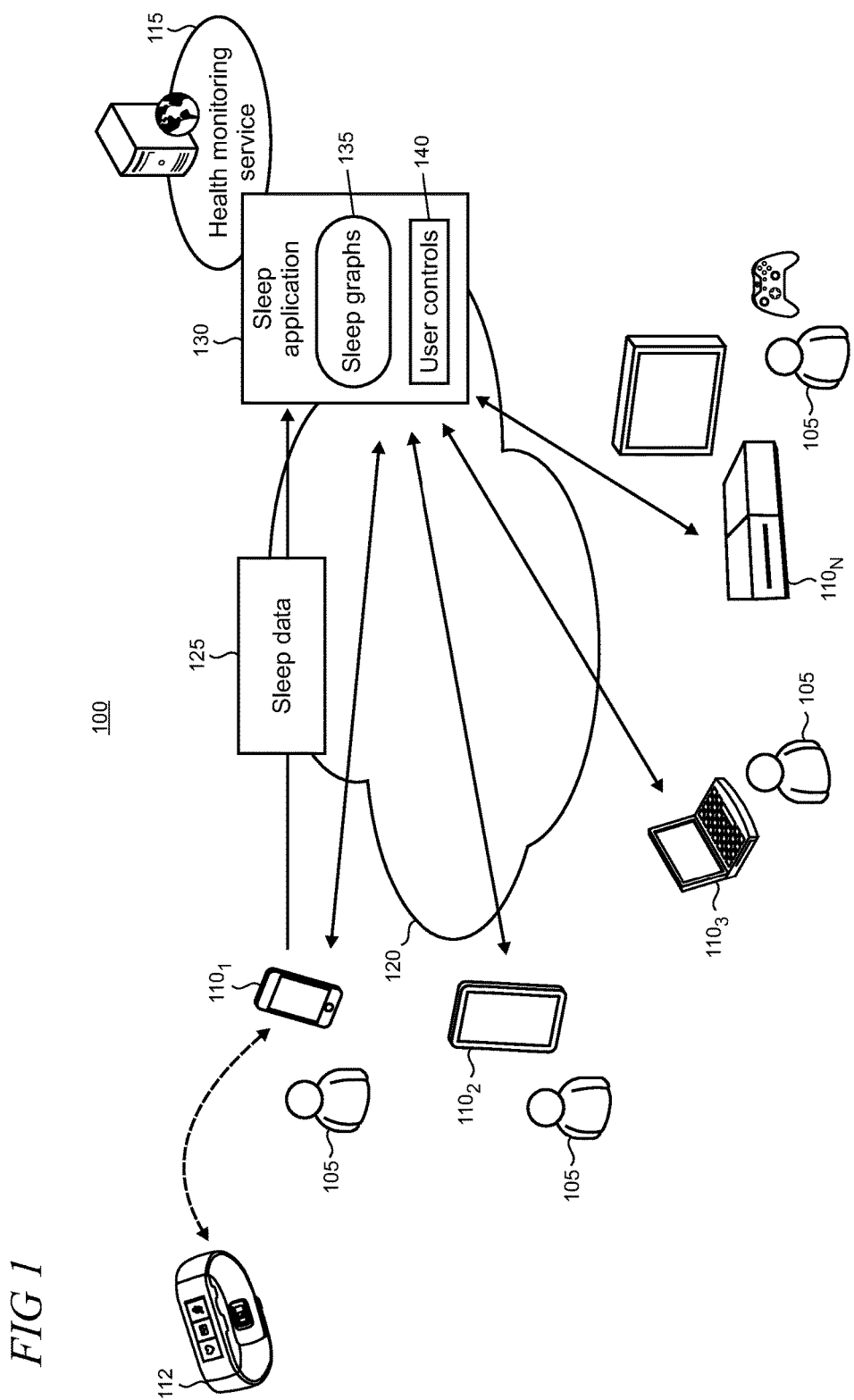
FIG. 1 shows an illustrative environment in which computing devices having communications capabilities interact with a health monitoring service over a network.

Like reference numerals indicate like elements in the drawings. Elements are not drawn to scale unless otherwise indicated. It is emphasized that the particular UIs displayed in the drawings can vary from what is shown according to the needs of a particular implementation. While UIs are shown in landscape mode in the drawings, the present arrangement may also be implemented using a portrait mode.

DETAILED DESCRIPTION

FIG. 1 shows an illustrative communications environment 100 in which one or more users 105 can employ various computing devices 110 to interact with a health monitoring service 115 over a communications network 120. Sleep data 125 that is associated with sleep behaviors of a user 105 is uploaded to a sleep application 130 that is exposed by the health monitoring service 115. The sleep application 130 provides sleep graphs 135 using the data 125 that can be accessed by the devices 110 over the network using, for example, a web browser or other suitable application. The sleep application 130 can also expose user controls 140 in some cases that enable a user 105 to control various aspects of the sleep graph generation and/or other features supported by the application. While this particular illustrative example describes a sleep application that supports optimized visibility of sleep sessions using the health monitoring service, in alternative implementations, a given device 110 can be adapted to provide the optimized visibility using sleep data and other resources and processing that are substantially locally implemented. For example, the sleep application can be configured as a locally executing application in some scenarios.

The devices 110 provide various capabilities and typically support data-consuming applications such as Internet browsing and multimedia (e.g., music, video, games) consumption in addition to various other features such as voice calling, and video calling and messaging in some cases. The devices 110 may include, for example, user equipment, mobile phones, smartphones, cell phones, feature phones, tablet computers, laptop PCs (personal computers), desktop computers, multimedia consoles, gaming systems, and smartphones which users often employ to participate in voice and/or multimedia (i.e., video) communications, engage in messaging (e.g., texting), use applications and access services that employ data, browse the World Wide Web, and the like.

Other types of electronic devices are also envisioned to be usable within the communications environment 100 so long as they are configured with communication capabilities and can connect to the communications network 120. Such alternative devices variously include handheld computing devices, PDAs (personal digital assistants), portable media players, phablet devices (i.e., combination smartphone/tablet devices), wearable computers, navigation devices such as GPS (Global Positioning System) systems, head mounted display (HMD) devices, embedded systems, smart appliances, or the like. In the discussion that follows, the use of the term "device" is intended to cover all devices that are configured with communication capabilities and are capable of connectivity to the communications network 120.

The communications network 120 can include any of a variety of network types and network infrastructure in various combinations or sub-combinations including cellular networks, satellite networks, IP (Internet Protocol) networks such as Wi-Fi and Ethernet networks, a public switched telephone network (PSTN), and/or short range networks such as Bluetooth® networks. The network infrastructure can be supported, for example, by mobile operators, enterprises, Internet service providers (ISPs), telephone service providers, data service providers, and the like.

An accessory device 112, such as a wristband or other wearable device, is also present in the environment 100. Such accessory device 112 typically is adapted to interoperate with a companion device 110 using a short range communication protocol to support functions such as monitoring of the wearer's physiology (e.g., heart rate, steps taken, calories burned) and environmental conditions (e.g., temperature, humidity, ultra-violet (UV) levels), and surfacing notifications from the coupled device 110.

Figure 2:
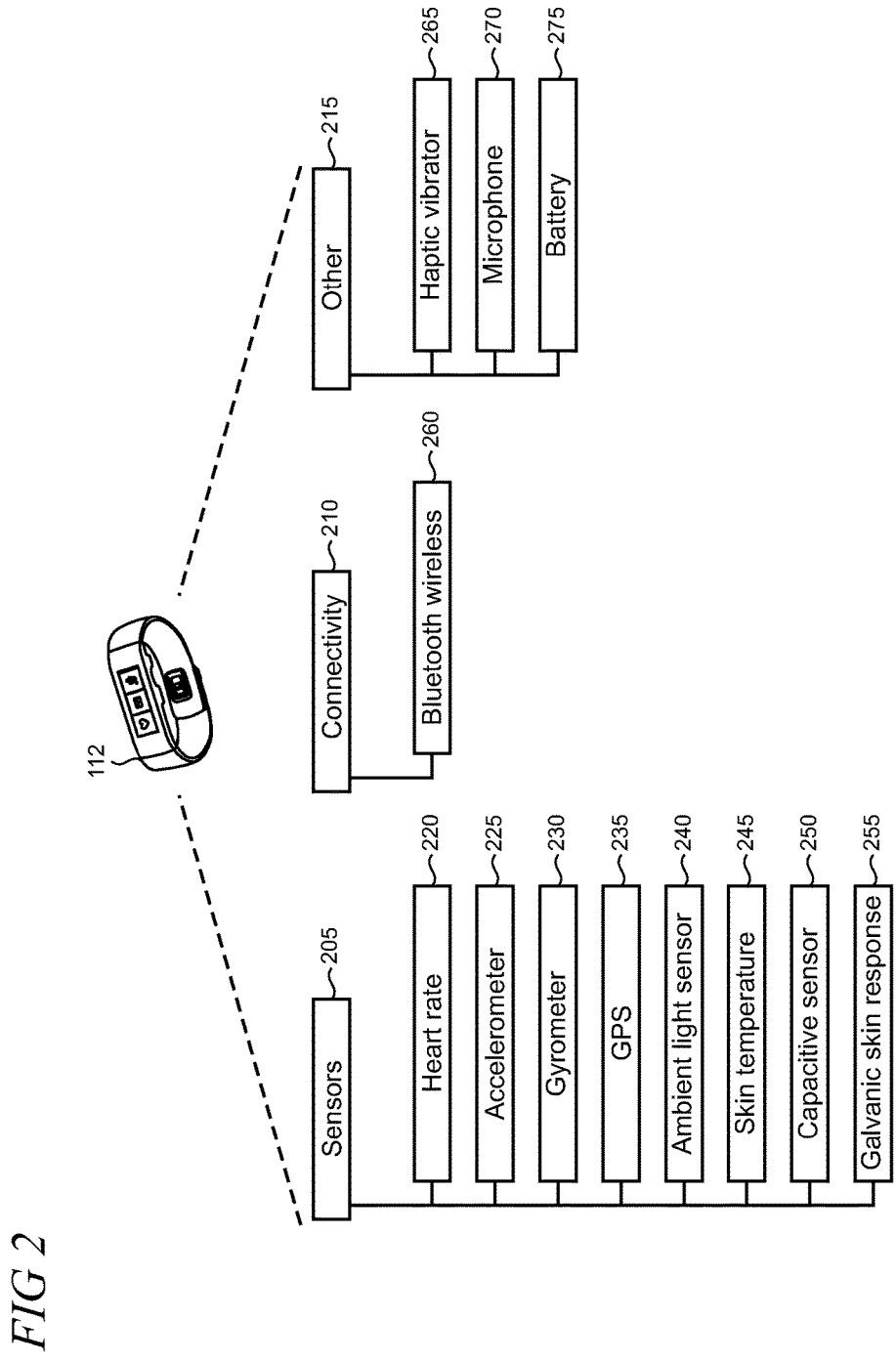
FIG. 2 shows illustrative components of a wearable device that provides sensor data used to generate sleep data.

FIG. 2 shows illustrative components of a wearable device that provides sensor data used to generate sleep data. The components in this example include sensors 205, connectivity components 210, and other components 215. The sensors 205 include a heart rate sensor 220; accelerometer 225; gyrometer gyroscope 230; a global positioning sensor 235 (such as a GPS (Global Positioning System) sensor, a Russian Global Navigation Satellite System (GLONASS) sensor, a Galileo positioning system sensor, an Indian Regional Navigation Satellite System sensor and a Chinese Beidou Navigation Satellite System sensor) 235; ambient light sensor 240; skin temperature sensor 245; capacitive sensor 250, and galvanic skin response sensor 255. In some cases, multiple sensor functionalities may be combined into a sensor and not all functionalities need to be implemented using discrete devices/components. The connectivity component 210 includes Bluetooth® wireless 260, or support for other suitable communication protocols, to enable interoperability with a companion device 110 such as a smartphone or tablet. Other components 215 include a haptic vibrator 265; microphone 270; and battery 275.

Figure 3:
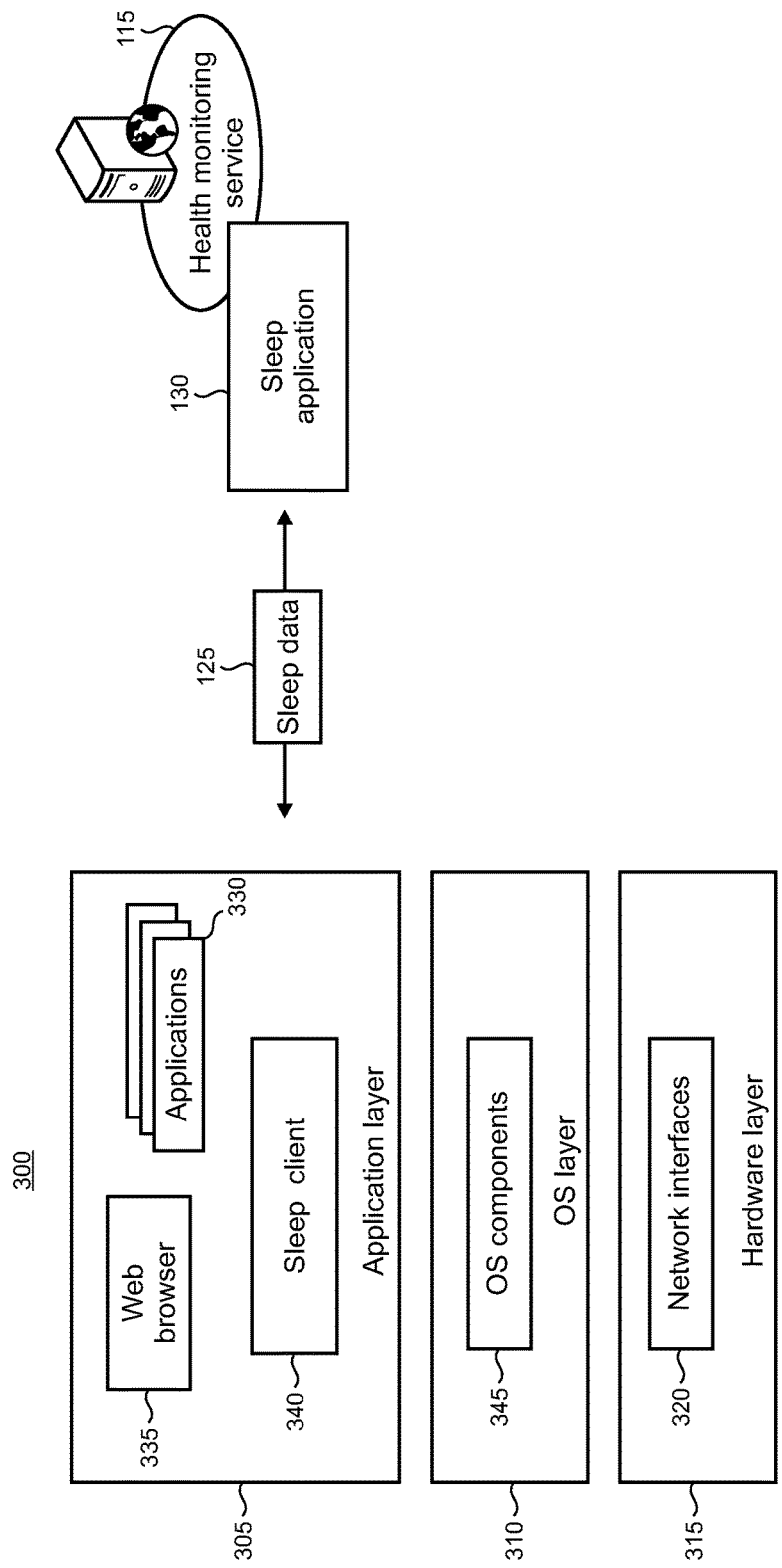
FIG. 3 shows an illustrative layered architecture instantiated on a computing device that includes a sleep client that interacts with a sleep application.

FIG. 3 shows an illustrative layered architecture 300 instantiated on a given device 110 that supports various applications and other components. The architecture 300 is typically implemented in software, although combinations of software, firmware, and/or hardware may also be utilized in some cases. The architecture 300 is arranged in layers and includes an application layer 305, an OS (operating system) layer 310, and a hardware layer 315. The hardware layer 315 provides an abstraction of various hardware used by the device 110 such as network interfaces 320, input and output devices, and radio hardware.

The application layer 305 in this illustrative example supports applications 330 (e.g., music player, email application, wearable device application), as well as a web browser 335. Some of the devices 110 may include a sleep client 340 that may interact with the sleep application 130 in order to facilitate the collection of sleep data 125. The applications in the application layer 305 are often implemented using locally executing code. However in some cases these applications may rely on services and/or remote code execution provided by remote servers or other computing platforms such as those supported by cloud-based resources/services. While the applications are shown here as components that are instantiated in the application layer 305, it may be appreciated that the functionality provided by a given application may be implemented, in whole or part, using OS components 345 and/or other components that are supported in the hardware layer 315.

Figure 4:
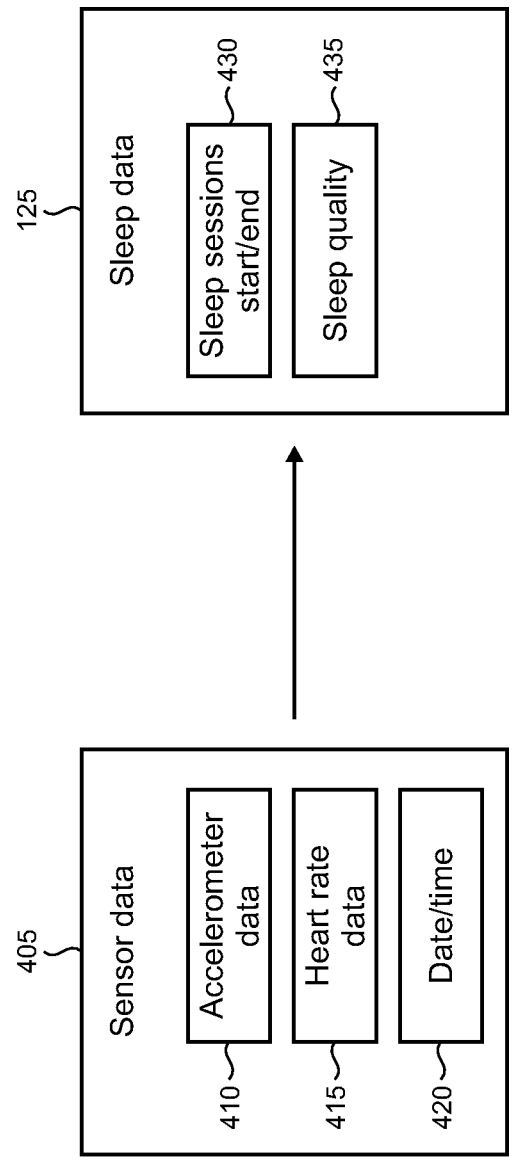
FIG. 4 shows sleep data that may be derived from sensor data.

The sleep data 125 may be derived from data obtained from the sensors 205 (FIG. 2) in the wearable device 112. As shown in FIG. 4 the sensor data 405 in this illustrative example includes accelerometer data 410, heart rate data 415, and date/time data 420. The sleep data 125 includes start and end times of sleep sessions 430 and some measure of sleep quality 435. In some scenarios, the sleep client 340 (FIG. 3) can pass raw sensor data to the sleep application 130 and the application derives the sleep data from the sensor data. In other scenarios, the sleep client can derive some or all of the sleep data locally and pass the sleep data to the sleep application over the communications network. It is emphasized that the sensor data and sleep data described here is intended to be illustrative and that other sensor data and sleep data may be utilized to meet the needs of a particular implementation.

Figure 5:
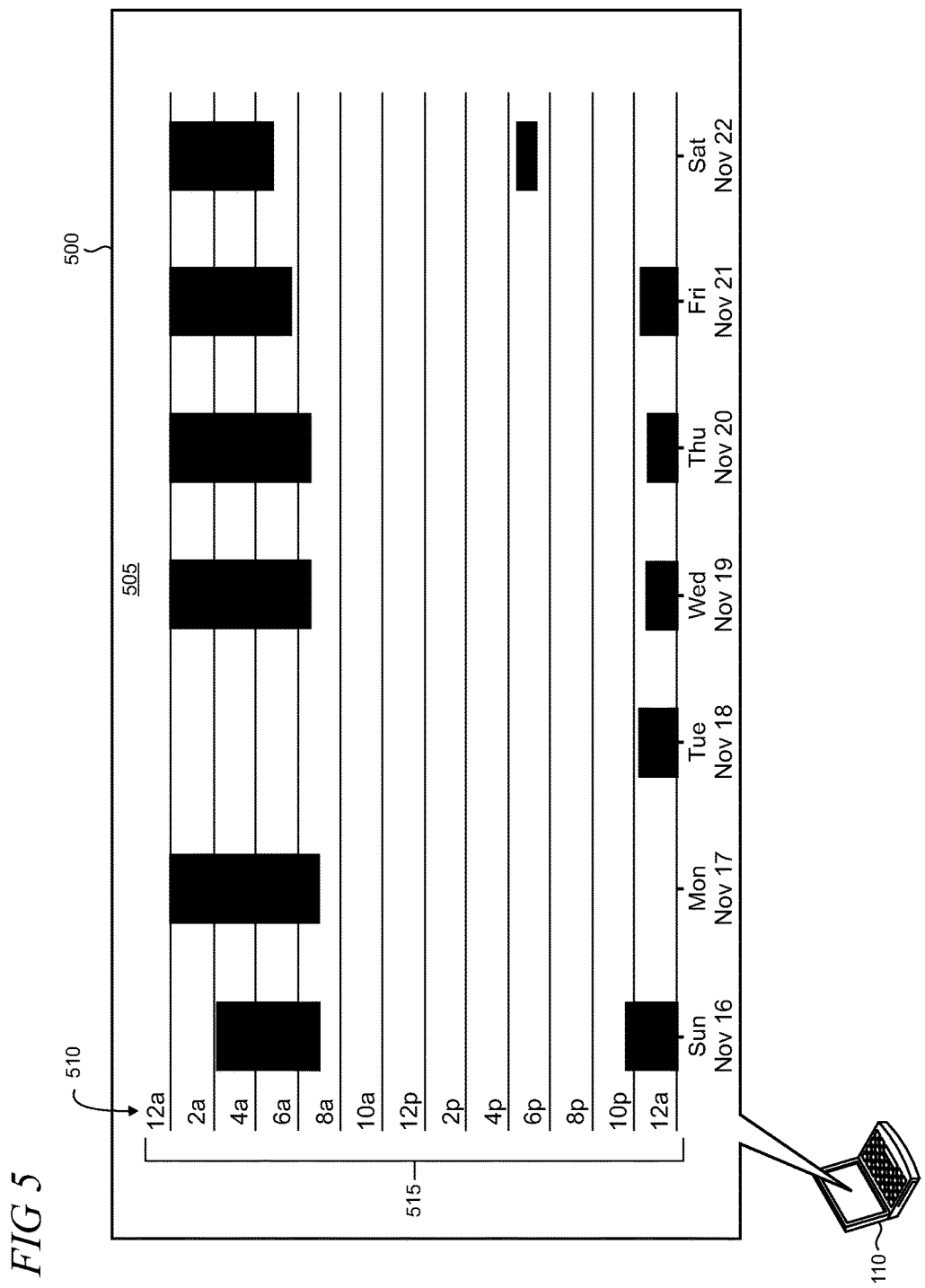
FIG. 5 shows a screen capture of an illustrative user interface that includes a graph of sleep sessions in which the time axis includes a 24 hour range starting at 12 midnight.

FIG. 5 shows a screen capture of an illustrative user interface (UI) 500 that includes a graph 505 of sleep sessions (shown using black bars) occurring over a calendar period of a week from Sunday through Saturday. As shown in the UI 500, the time axis 510 includes a 24 hour range 515 starting at 12 am at the top of the graph. Configuring the range 515 to start at 12 am may be considered logical because the day starts at 12 am. However, using this particular range breaks the sleep session bars in the graph so they are not continuous (as most sleep sessions start before midnight and end the following day), which can make comprehension of the graph difficult for the user. It can be difficult to compare amounts of sleep on different days quickly because it requires the user to mentally add the broken bars together. The graph 505 also does not utilize UI space efficiently as it contains a lot of empty space that is centrally located in the graph and pushes the pertinent sleep session representations to the top and bottom of the graph where it is less prominent.

A graphing process utilized by the sleep application 130 provides optimized visibility for the sleep sessions by calculating a range for the time axis using a start time that enables the graph to include the most continuous (i.e., non-broken) sleep sessions.

Figure 6:
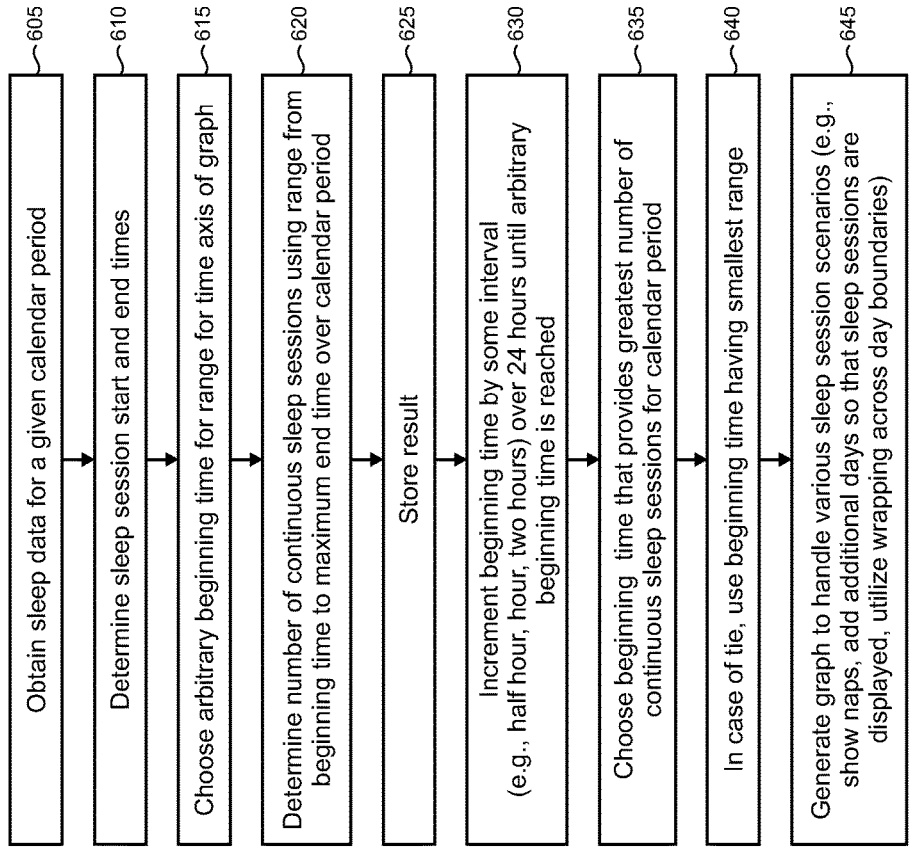
FIG. 6 shows an illustrative graphing process that may be performed by the sleep application.

An illustrative graphing process 600 is shown in FIG. 6. In step 605, sleep data is obtained over some calendar period of interest. For example, sleep sessions can be generated and rendered for a day, several days, a week, a month, several months, or other calendar periods to suit a particular implementation. In step 610, sleep session start and end times are determined.

An arbitrary beginning time for the range for the time axis of the graph is chosen in step 615. Typically, the times shown in the range are at the top of an hour (e.g., 10 pm, 11 pm), but other times can also be utilized (10:30 pm, 11:30 pm). In step 620, the number of continuous sleep sessions over the range from the chosen beginning time to a maximum end time is determined and the result is stored in step 625. In step 630, the beginning time for the range is incremented by some interval (e.g., half hour, hour, two hours) and steps 620 and 625 (determining and storing) are iterated for a full 24 hours until the initial arbitrary beginning time is reached. Thus, for example, the process can start at 4 pm for the beginning of the range and determine the number of continuous sleep sessions determined for that time. The number of continuous sleep sessions for a range beginning at 5 pm is next determined, and so on for each of the hours in the day.

In step 635, a beginning time for the range is chosen from all of the stored beginning times results that provides the greatest number of continuous sleep sessions for the calendar period. In step 640, in a case of a tie, the beginning time that results in the smallest range is utilized. Using the beginning time with the smallest range reduces empty space on the graph and maximizes the scaling of graphed sleep sessions that are smaller, such as naps. As shown in step 645, the graphing process then generates the sleep graphs that can be accessed by the device 110 (FIG. 1) over the network 120.

In some cases the graphs can accommodate various sleep session scenarios such as naps, utilize wrapping across days, and employ additional days to ensure that sleep sessions are rendered and not lost as needed in some cases. For example, the graphing process can expand the range on the time axis up to 24 hours as needed. If there are any sleep sessions that cannot be fit unbroken within the expanded range, then those sleep sessions can be wrapped across a day boundary and be rendered using two bars. The graphing process can also place an additional day in a graph at a beginning or end of the calendar period when needed (as shown in FIG. 9 and described in the accompanying text below).

Figure 7:
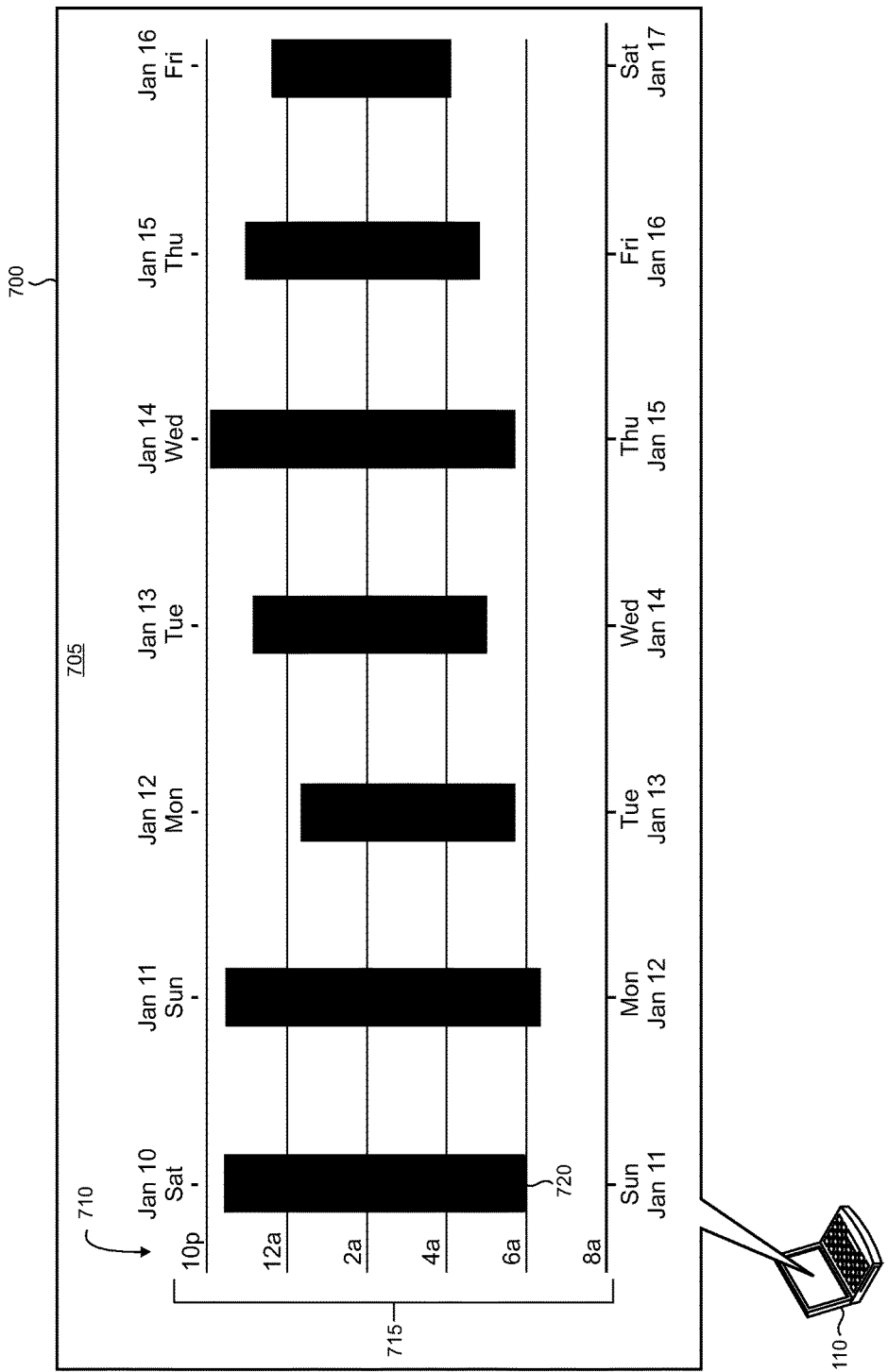
FIGS. 7, 8, 9, and 10 show screen captures of illustrative user interfaces (UIs) supported by a device when accessing the sleep application.

FIGS. 7, 8, 9, and 10 show screen captures of illustrative UIs supported by a device, for example using a web browser, when accessing the sleep application 130 over the communications network 120. The illustrative UI 700 in FIG. 7 shows the results of application of the graphing process 600 (FIG. 6). As shown, the range 715 on the time axis 710 begins at 10 pm on one day and ends at 8 am the following day. The selection of this range enables each of the seven sleep sessions (representatively indicated by reference numeral 720) across the time span of a week to be visible in a continuous manner without breaks where the data is substantially centered in the graph 705. The graph depicts the sleep sessions so that the user can conveniently see his or her bed times and wake up times at a glance over the calendar period. In addition, the size of the continuous sleep session bars can be readily compared so that the user can graphically ascertain the amount of sleep the user is getting on any particular day.

Figure 8:
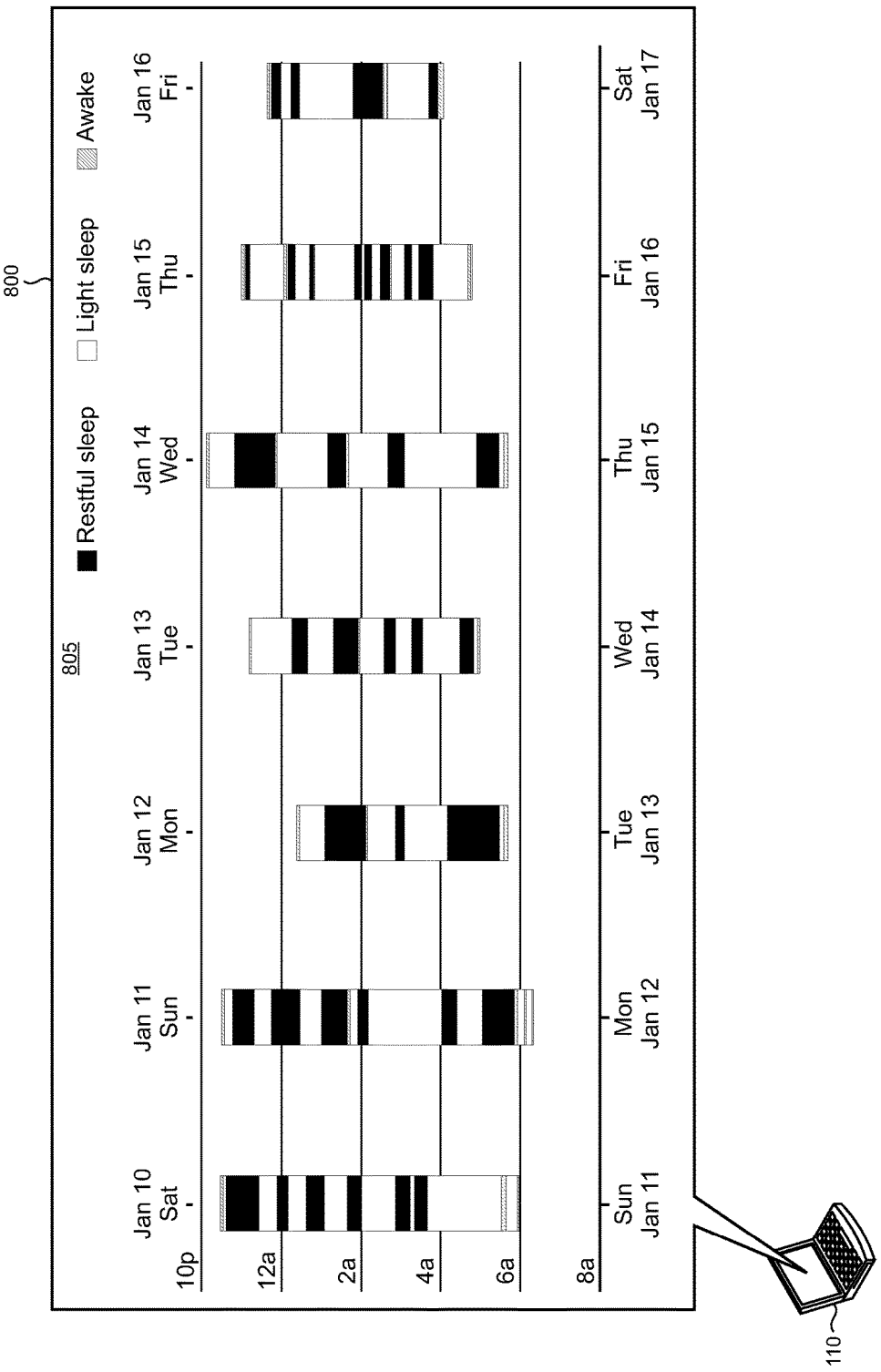

FIG. 8 shows an illustrative UI 800 in which the sleep session bars in the graph 805 are graphically encoded to show sleep quality. In this example, the bars show light sleep, deeper restful sleep, and waking states over the course of each sleep session. Sleep quality may be inferred using the sleep data obtained from the client application, for example, by observing user heart rate and correlating user movements detected by the accelerometer in the wearable device 112 (FIGS. 1 and 2).

Figure 9:
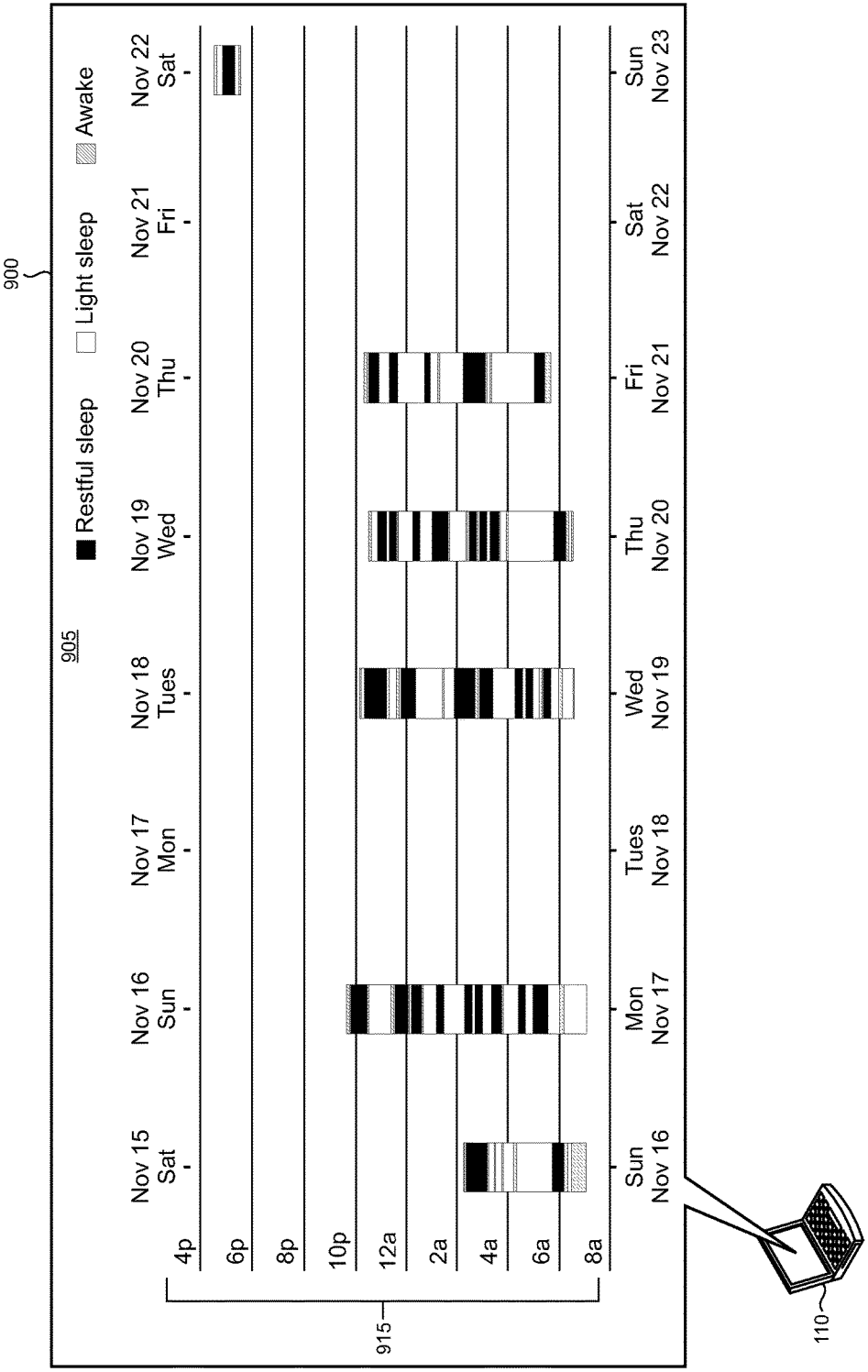

FIG. 9 shows an illustrative UI 900 in which the graphing process 600 (FIG. 6) adjusts the graph 905 to use a range 915 that is configured to show a short duration sleep session (e.g., a nap). In addition, the graphing process adds another day (Saturday, November 15 to Sunday, November 16) to display a sleep session starting around 2 am Saturday morning that would otherwise not be displayed since the graphed range runs from 4 pm to 8 am.

Figure 10:
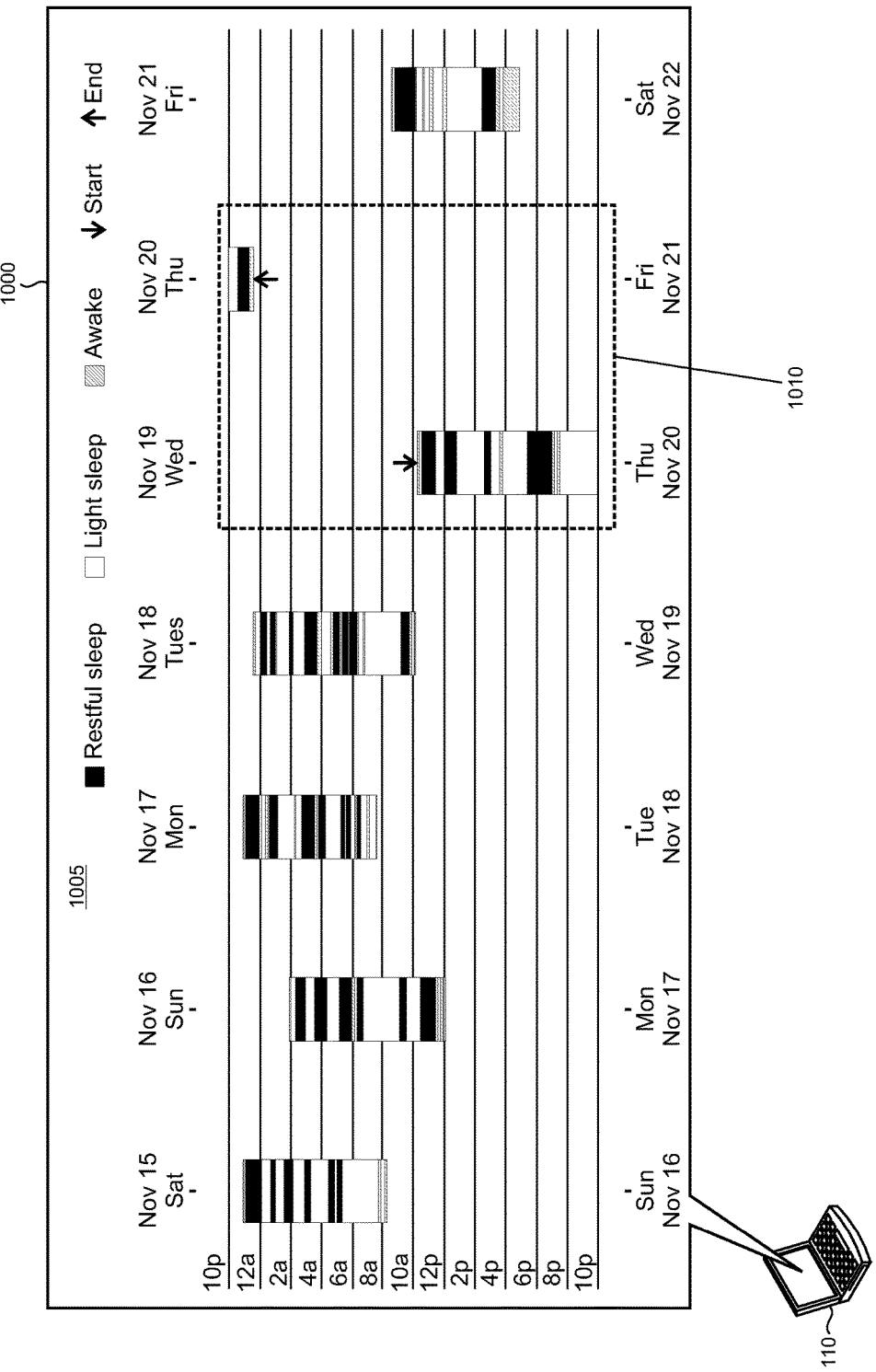

FIG. 10 shows an illustrative UI 1000 in which the graphing process 600 (FIG. 6) adjusts the graph 1005 to wrap a sleep session across day boundaries on the graph. As shown, a sleep session indicated by the dashed rectangle 1010 spans the boundary between Wednesday/Thursday and Thursday/Friday on the graph. The start and end of the wrapped sleep session is graphically indicated using start and end arrows.

Figure 11:
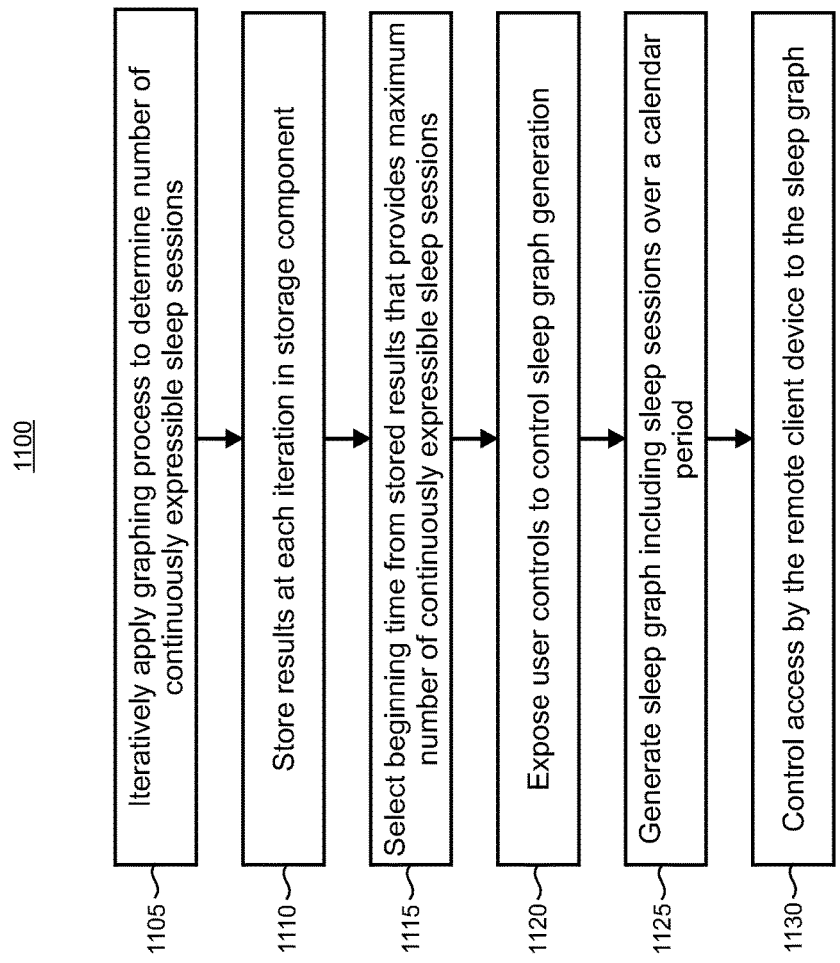
FIGS. 11, 12, and 13 show illustrative methods that may be performed when implementing the present optimized visibility for sleep sessions.
Figure 12:
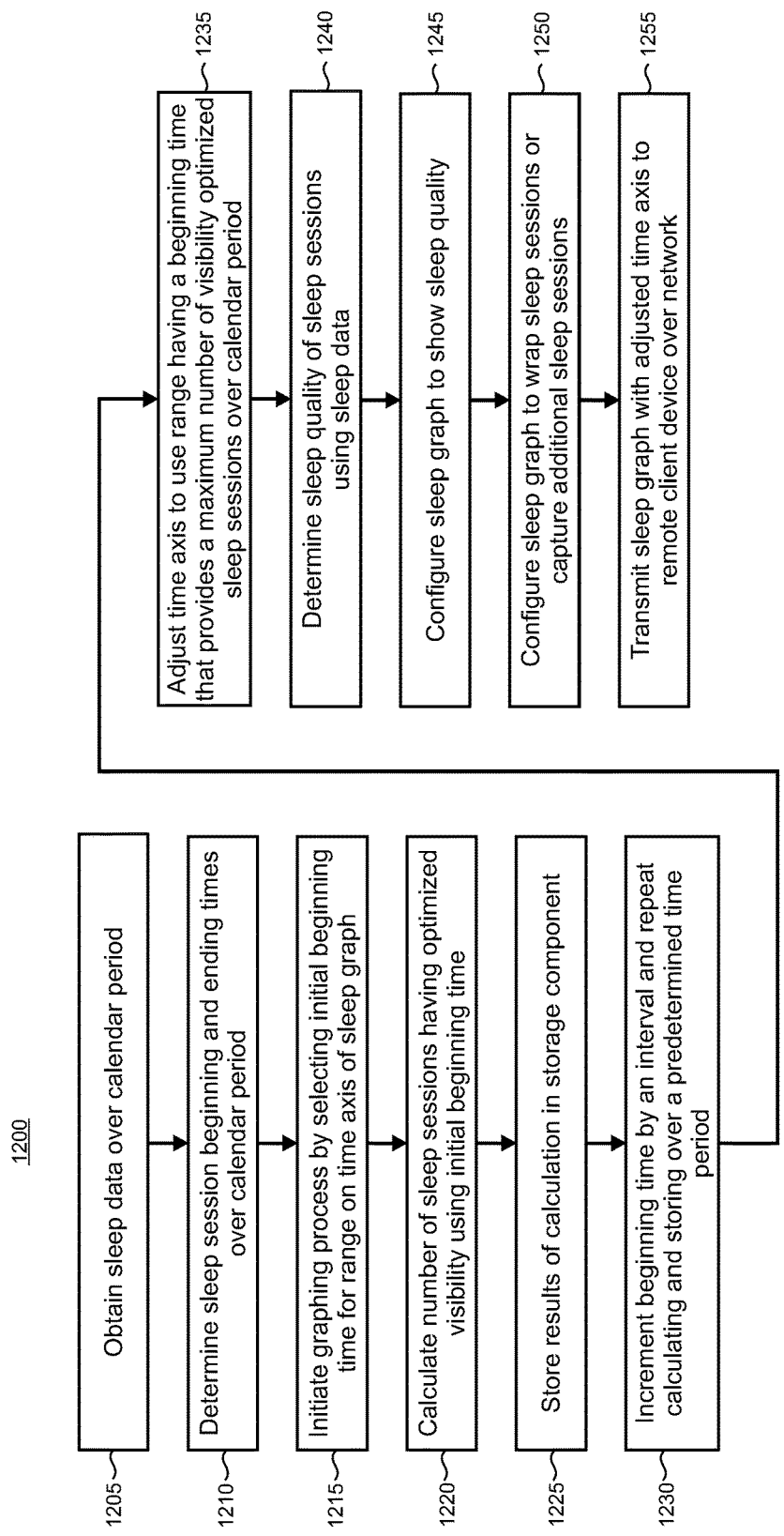
Figure 13:
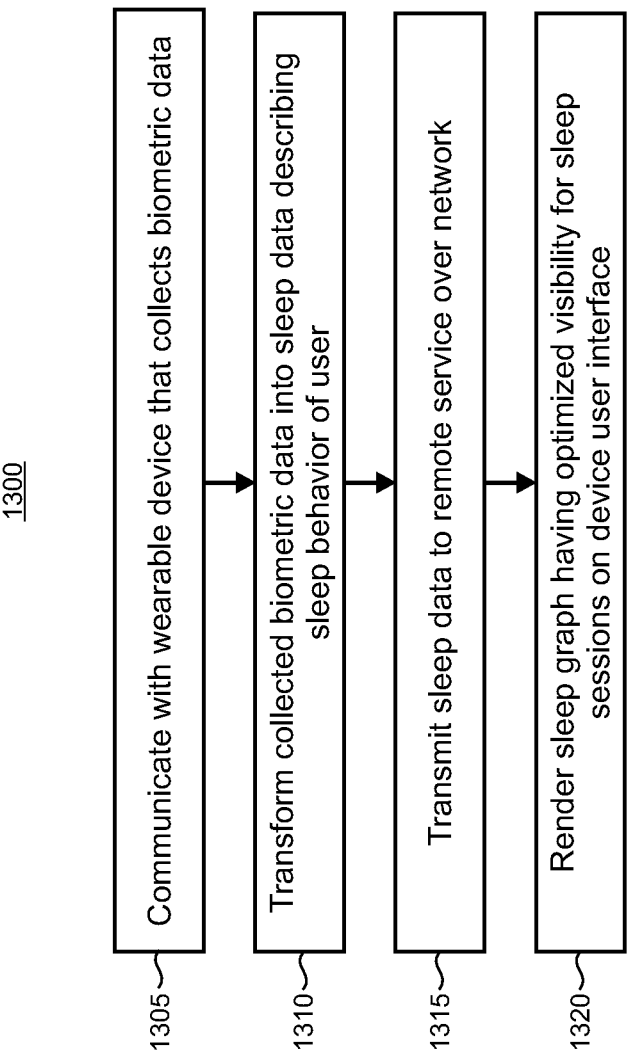

FIGS. 11, 12, and 13 show illustrative methods that may be performed when implementing the present optimized visibility for sleep sessions. Unless specifically stated, the methods or steps shown in the flowcharts below and described in the accompanying text are not constrained to a particular order or sequence. In addition, some of the methods or steps thereof can occur or be performed concurrently and not all the methods or steps have to be performed in a given implementation depending on the requirements of such implementation and some methods or steps may be optionally utilized.

The illustrative method 1100 in FIG. 11 may be performed on a computer server or other computing platform that is associated with the health monitoring service 115 (FIG. 1). In step 1105, a graphing process (e.g., graphing process 600 shown in FIG. 6 and described in the accompanying text) is iteratively applied for different beginning times for a sleep graph's time axis range to determine a number of continuously expressible sleep sessions. The results for each of the iterations are stored in a storage component in step 1110.

In step 1115, a beginning time is selected from the stored results that provides a maximum number of continuously expressible sleep sessions. In some implementations, user controls that enable control of sleep graph generation are exposed to a remote client device in step 1120. In step 1125, a sleep graph is generated that includes sleep sessions over a calendar period. Access to the generated sleep graph by the remote client device is controlled in step 1130.

The illustrative method 1200 in FIG. 12 may be performed by the health monitoring service 115 (FIG. 1). In step 1205, sleep data is obtained over a calendar period (e.g., a week, month, year), for example by receiving data collected from a companion device that is operatively coupled to a wearable or other device that includes health monitoring or biometric sensors. In step 1210, sleep session starting and ending times over the calendar period are determined from the sleep data. The graphing process (e.g., graphing process 600 shown in FIG. 6 and described in the accompanying text) is initiated in step 1215 by selecting an initial beginning time for the range on the time axis of the sleep graph.

In step 1220, the number of sleeps sessions having optimized visibility is calculated using the initial beginning time and the calculation result is stored in a storage component in step 1225. The beginning time is incremented by some interval (e.g., an hour) and the calculating and storage of the calculation result is repeated over some predetermined time period (e.g., a 24 hour time period) in step 1230. In step 1235, the time axis of the sleep graph is adjusted to use a range having a beginning time that provides a maximum number of visibility optimized sleep sessions over the calendar period.

In step 1240, in some implementations, a sleep quality of the sleep sessions is determined using the sleep data and the sleep graph may be configured to show the sleep quality in step 1245. The sleep graph may also be configured in some cases to wrap sleep sessions across calendar boundaries and/or capture additional sleep sessions in step 1250. In step 1255, the sleep graph may be transmitted to a remote client device over a network.

Illustrative method 1300 in FIG. 13 may be performed by a computing device that is operatively coupled to a wearable device that is configured to collect biometric data from a wearable device user. In step 1305, communication is implemented with the wearable device, for example using a short range communication protocol such as Bluetooth® or some other suitable protocol. In step 1310, the collected biometric data is transformed into sleep data that describes sleep behavior of the user. In step 1315, the sleep data can be optionally transmitted to a remote service (e.g., the health monitoring service 115 shown in FIG. 1 and described in the accompanying text) over a network. In step 1320, a sleep graph having optimized visibility for sleep sessions can be rendered on a UI supported by the device. In some cases, the sleep graph can be generated locally on the device, while in other cases the sleep graph can be generated by the remote service using the transmitted sleep data.

Figure 14:
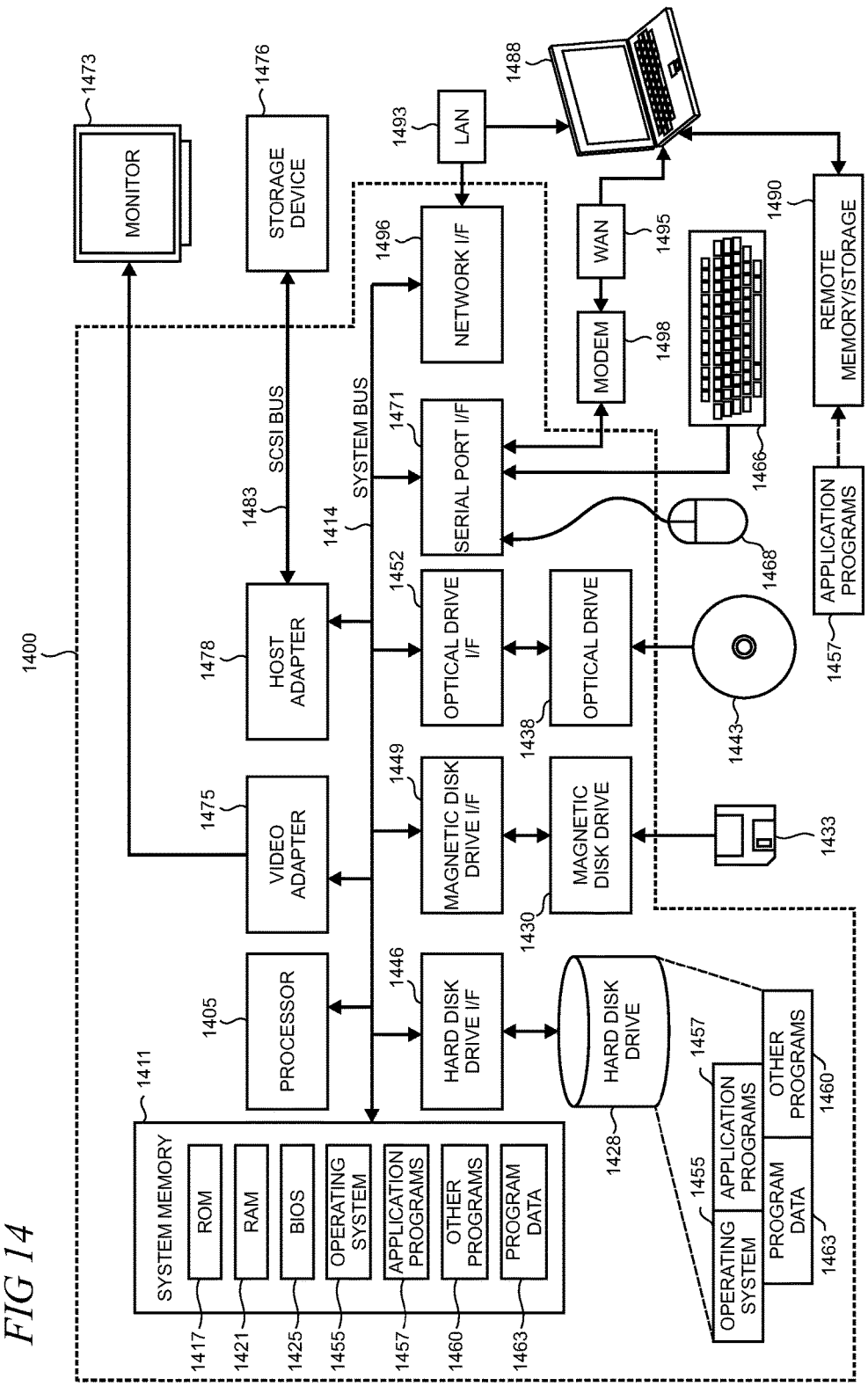
FIG. 14 is a simplified block diagram of an illustrative computer system such as a personal computer (PC) that may be used in part to implement the present optimized visibility for sleep sessions.

FIG. 14 is a simplified block diagram of an illustrative computer system 1400 such as a PC, client machine, or server with which the present optimized visibility for sleep sessions over time may be implemented. Computer system 1400 includes a processor 1405, a system memory 1411, and a system bus 1414 that couples various system components including the system memory 1411 to the processor 1405. The system bus 1414 may be any of several types of bus structures including a memory bus or memory controller, a peripheral bus, or a local bus using any of a variety of bus architectures. The system memory 1411 includes read only memory (ROM) 1417 and random access memory (RAM) 1421. A basic input/output system (BIOS) 1425, containing the basic routines that help to transfer information between elements within the computer system 1400, such as during startup, is stored in ROM 1417. The computer system 1400 may further include a hard disk drive 1428 for reading from and writing to an internally disposed hard disk (not shown), a magnetic disk drive 1430 for reading from or writing to a removable magnetic disk 1433 (e.g., a floppy disk), and an optical disk drive 1438 for reading from or writing to a removable optical disk 1443 such as a CD (compact disc), DVD (digital versatile disc), or other optical media. The hard disk drive 1428, magnetic disk drive 1430, and optical disk drive 1438 are connected to the system bus 1414 by a hard disk drive interface 1446, a magnetic disk drive interface 1449, and an optical drive interface 1452, respectively. The drives and their associated computer-readable storage media provide non-volatile storage of computer-readable instructions, data structures, program modules, and other data for the computer system 1400. Although this illustrative example includes a hard disk, a removable magnetic disk 1433, and a removable optical disk 1443, other types of computer-readable storage media which can store data that is accessible by a computer such as magnetic cassettes, Flash memory cards, digital video disks, data cartridges, random access memories (RAMs), read only memories (ROMs), and the like may also be used in some applications of the present optimized visibility for sleep sessions over time. In addition, as used herein, the term computer-readable storage media includes one or more instances of a media type (e.g., one or more magnetic disks, one or more CDs). For purposes of this specification and the claims, the phrase "computer-readable storage media" and variations thereof, does not include waves, signals, and/or other transitory and/or intangible communication media.

A number of program modules may be stored on the hard disk, magnetic disk 1433, optical disk 1443, ROM 1417, or RAM 1421, including an operating system 1455, one or more application programs 1457, other program modules 1460, and program data 1463. A user may enter commands and information into the computer system 1400 through input devices such as a keyboard 1466 and pointing device 1468 such as a mouse. Other input devices (not shown) may include a microphone, joystick, game pad, satellite dish, scanner, trackball, touchpad, touch screen, touch-sensitive device, voice-command module or device, user motion or user gesture capture device, or the like. These and other input devices are often connected to the processor 1405 through a serial port interface 1471 that is coupled to the system bus 1414, but may be connected by other interfaces, such as a parallel port, game port, or universal serial bus (USB). A monitor 1473 or other type of display device is also connected to the system bus 1414 via an interface, such as a video adapter 1475. In addition to the monitor 1473, personal computers typically include other peripheral output devices (not shown), such as speakers and printers. The illustrative example shown in FIG. 14 also includes a host adapter 1478, a Small Computer System Interface (SCSI) bus 1483, and an external storage device 1476 connected to the SCSI bus 1483.

The computer system 1400 is operable in a networked environment using logical connections to one or more remote computers, such as a remote computer 1488. The remote computer 1488 may be selected as another personal computer, a server, a router, a network PC, a peer device, or other common network node, and typically includes many or all of the elements described above relative to the computer system 1400, although only a single representative remote memory/storage device 1490 is shown in FIG. 14. The logical connections depicted in FIG. 14 include a local area network (LAN) 1493 and a wide area network (WAN) 1495. Such networking environments are often deployed, for example, in offices, enterprise-wide computer networks, intranets, and the Internet.

When used in a LAN networking environment, the computer system 1400 is connected to the local area network 1493 through a network interface or adapter 1496. When used in a WAN networking environment, the computer system 1400 typically includes a broadband modem 1498, network gateway, or other means for establishing communications over the wide area network 1495, such as the Internet. The broadband modem 1498, which may be internal or external, is connected to the system bus 1414 via a serial port interface 1471. In a networked environment, program modules related to the computer system 1400, or portions thereof, may be stored in the remote memory storage device 1490. It is noted that the network connections shown in FIG. 14 are illustrative and other means of establishing a communications link between the computers may be used depending on the specific requirements of an application of the present optimized visibility for sleep sessions over time.

Figure 15:
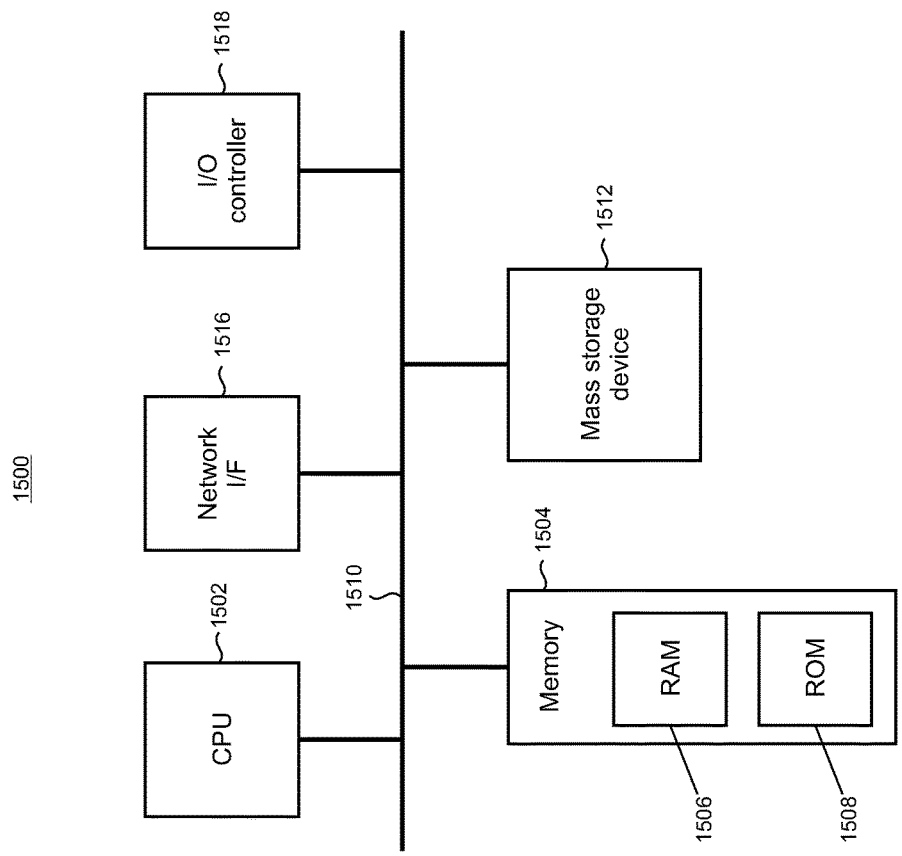
FIG. 15 shows a block diagram of an illustrative system that may be used in part to implement the present optimized visibility for sleep sessions.

FIG. 15 shows an illustrative architecture 1500 for a device capable of executing the various components described herein for providing the present optimized visibility for sleep sessions over time. Thus, the architecture 1500 illustrated in FIG. 15 shows an architecture that may be adapted for a server computer, mobile phone, a PDA, a smartphone, a desktop computer, a netbook computer, a tablet computer, GPS device, gaming console, and/or a laptop computer. The architecture 1500 may be utilized to execute any aspect of the components presented herein.

The architecture 1500 illustrated in FIG. 15 includes a CPU (Central Processing Unit) 1502, a system memory 1504, including a RAM 1506 and a ROM 1508, and a system bus 1510 that couples the memory 1504 to the CPU 1502. A basic input/output system containing the basic routines that help to transfer information between elements within the architecture 1500, such as during startup, is stored in the ROM 1508. The architecture 1500 further includes a mass storage device 1512 for storing software code or other computer-executed code that is utilized to implement applications, the file system, and the operating system.

The mass storage device 1512 is connected to the CPU 1502 through a mass storage controller (not shown) connected to the bus 1510. The mass storage device 1512 and its associated computer-readable storage media provide non-volatile storage for the architecture 1500.

Although the description of computer-readable storage media contained herein refers to a mass storage device, such as a hard disk or CD-ROM drive, it may be appreciated by those skilled in the art that computer-readable storage media can be any available storage media that can be accessed by the architecture 1500.

By way of example, and not limitation, computer-readable storage media may include volatile and non-volatile, removable and non-removable media implemented in any method or technology for storage of information such as computer-readable instructions, data structures, program modules, or other data. For example, computer-readable media includes, but is not limited to, RAM, ROM, EPROM (erasable programmable read only memory), EEPROM (electrically erasable programmable read only memory), Flash memory or other solid state memory technology, CD-ROM, DVDs, HD-DVD (High Definition DVD), Blu-ray, or other optical storage, magnetic cassettes, magnetic tape, magnetic disk storage or other magnetic storage devices, or any other medium which can be used to store the desired information and which can be accessed by the architecture 1500.

According to various embodiments, the architecture 1500 may operate in a networked environment using logical connections to remote computers through a network. The architecture 1500 may connect to the network through a network interface unit 1516 connected to the bus 1510. It may be appreciated that the network interface unit 1516 also may be utilized to connect to other types of networks and remote computer systems. The architecture 1500 also may include an input/output controller 1518 for receiving and processing input from a number of other devices, including a keyboard, mouse, or electronic stylus (not shown in FIG. 15). Similarly, the input/output controller 1518 may provide output to a display screen, a printer, or other type of output device (also not shown in FIG. 15).

It may be appreciated that the software components described herein may, when loaded into the CPU 1502 and executed, transform the CPU 1502 and the overall architecture 1500 from a general-purpose computing system into a special-purpose computing system customized to facilitate the functionality presented herein. The CPU 1502 may be constructed from any number of transistors or other discrete circuit elements, which may individually or collectively assume any number of states. More specifically, the CPU 1502 may operate as a finite-state machine, in response to executable instructions contained within the software modules disclosed herein. These computer-executable instructions may transform the CPU 1502 by specifying how the CPU 1502 transitions between states, thereby transforming the transistors or other discrete hardware elements constituting the CPU 1502.

Encoding the software modules presented herein also may transform the physical structure of the computer-readable storage media presented herein. The specific transformation of physical structure may depend on various factors, in different implementations of this description. Examples of such factors may include, but are not limited to, the technology used to implement the computer-readable storage media, whether the computer-readable storage media is characterized as primary or secondary storage, and the like. For example, if the computer-readable storage media is implemented as semiconductor-based memory, the software disclosed herein may be encoded on the computer-readable storage media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable storage media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media to change the optical characteristics of those locations. Other transformations of physical media are possible without departing from the scope and spirit of the present description, with the foregoing examples provided only to facilitate this discussion.

In light of the above, it may be appreciated that many types of physical transformations take place in the architecture 1500 in order to store and execute the software components presented herein. It may also be appreciated that the architecture 1500 may include other types of computing devices, including handheld computers, embedded computer systems, smartphones, PDAs, and other types of computing devices known to those skilled in the art. It is also contemplated that the architecture 1500 may not include all of the components shown in FIG. 15, may include other components that are not explicitly shown in FIG. 15, or may utilize an architecture completely different from that shown in FIG. 15.

Figure 16:
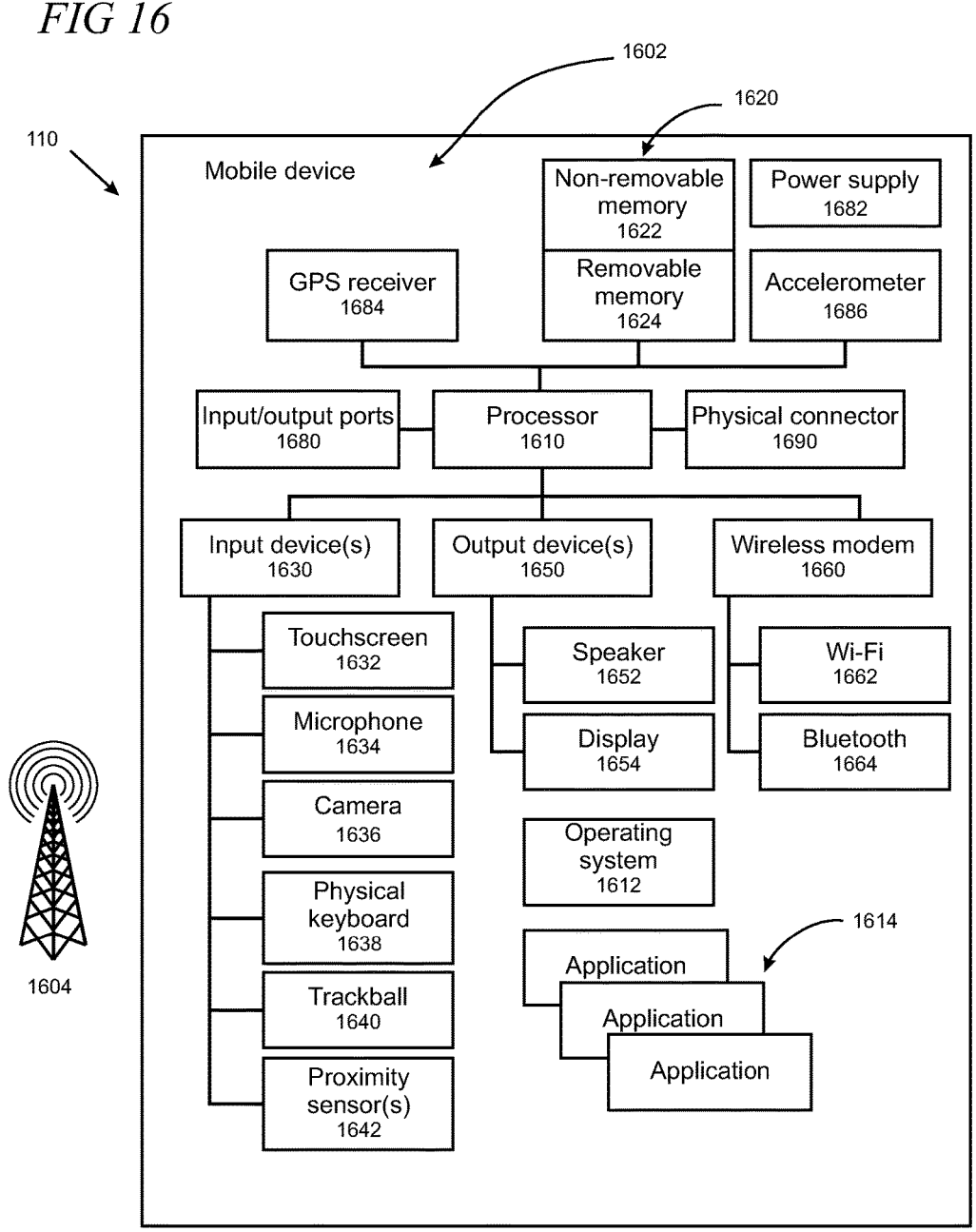
FIG. 16 is a block diagram of an illustrative mobile device.

FIG. 16 is a functional block diagram of an illustrative mobile device 110 such as a mobile phone or smartphone including a variety of optional hardware and software components, shown generally at 1602. Any component 1602 in the mobile device can communicate with any other component, although, for ease of illustration, not all connections are shown. The mobile device can be any of a variety of computing devices (e.g., cell phone, smartphone, handheld computer, PDA) and can allow wireless two-way communications with one or more mobile communication networks 1604, such as a cellular or satellite network.

The illustrated device 110 can include a controller or processor 1610 (e.g., signal processor, microprocessor, microcontroller, ASIC (Application Specific Integrated Circuit), or other control and processing logic circuitry) for performing such tasks as signal coding, data processing, input/output processing, power control, and/or other functions. An operating system 1612 can control the allocation and usage of the components 1602, including power states, above-lock states, and below-lock states, and provides support for one or more application programs 1614. The application programs can include common mobile computing applications (e.g., image-capture applications, email applications, calendars, contact managers, web browsers, messaging applications), or any other computing application.

The illustrated mobile device 110 can include memory 1620. Memory 1620 can include non-removable memory 1622 and/or removable memory 1624. The non-removable memory 1622 can include RAM, ROM, Flash memory, a hard disk, or other well-known memory storage technologies. The removable memory 1624 can include Flash memory or a Subscriber Identity Module (SIM) card, which is well known in GSM (Global System for Mobile communications) systems, or other well-known memory storage technologies, such as "smart cards." The memory 1620 can be used for storing data and/or code for running the operating system 1612 and the application programs 1614. Example data can include web pages, text, images, sound files, video data, or other data sets to be sent to and/or received from one or more network servers or other devices via one or more wired or wireless networks.

The memory 1620 may also be arranged as, or include, one or more computer-readable storage media implemented in any method or technology for storage of information such as computer-readable instructions, data structures, program modules or other data. For example, computer-readable media includes, but is not limited to, RAM, ROM, EPROM, EEPROM, Flash memory or other solid state memory technology, CD-ROM (compact-disc ROM), DVD, (Digital Versatile Disc) HD-DVD (High Definition DVD), Blu-ray, or other optical storage, magnetic cassettes, magnetic tape, magnetic disk storage or other magnetic storage devices, or any other medium which can be used to store the desired information and which can be accessed by the mobile device 110.

The memory 1620 can be used to store a subscriber identifier, such as an International Mobile Subscriber Identity (IMSI), and an equipment identifier, such as an International Mobile Equipment Identifier (IMEI). Such identifiers can be transmitted to a network server to identify users and equipment. The mobile device 110 can support one or more input devices 1630; such as a touch screen 1632; microphone 1634 for implementation of voice input for voice recognition, voice commands and the like; camera 1636; physical keyboard 1638; trackball 1640; and/or proximity sensor 1642; and one or more output devices 1650, such as a speaker 1652 and one or more displays 1654. Other input devices (not shown) using gesture recognition may also be utilized in some cases. Other possible output devices (not shown) can include piezoelectric or haptic output devices. Some devices can serve more than one input/output function. For example, touchscreen 1632 and display 1654 can be combined into a single input/output device.

A wireless modem 1660 can be coupled to an antenna (not shown) and can support two-way communications between the processor 1610 and external devices, as is well understood in the art. The modem 1660 is shown generically and can include a cellular modem for communicating with the mobile communication network 1604 and/or other radio-based modems (e.g., Bluetooth 1664 or Wi-Fi 1662). The wireless modem 1660 is typically configured for communication with one or more cellular networks, such as a GSM network for data and voice communications within a single cellular network, between cellular networks, or between the mobile device and a public switched telephone network (PSTN).

The mobile device can further include at least one input/output port 1680, a power supply 1682, a satellite navigation system receiver 1684, such as a GPS receiver, an accelerometer 1686, a gyroscope (not shown), and/or a physical connector 1690, which can be a USB port, IEEE 1394 (FireWire) port, and/or an RS-232 port. The illustrated components 1602 are not required or all-inclusive, as any components can be deleted and other components can be added.

Figure 17:
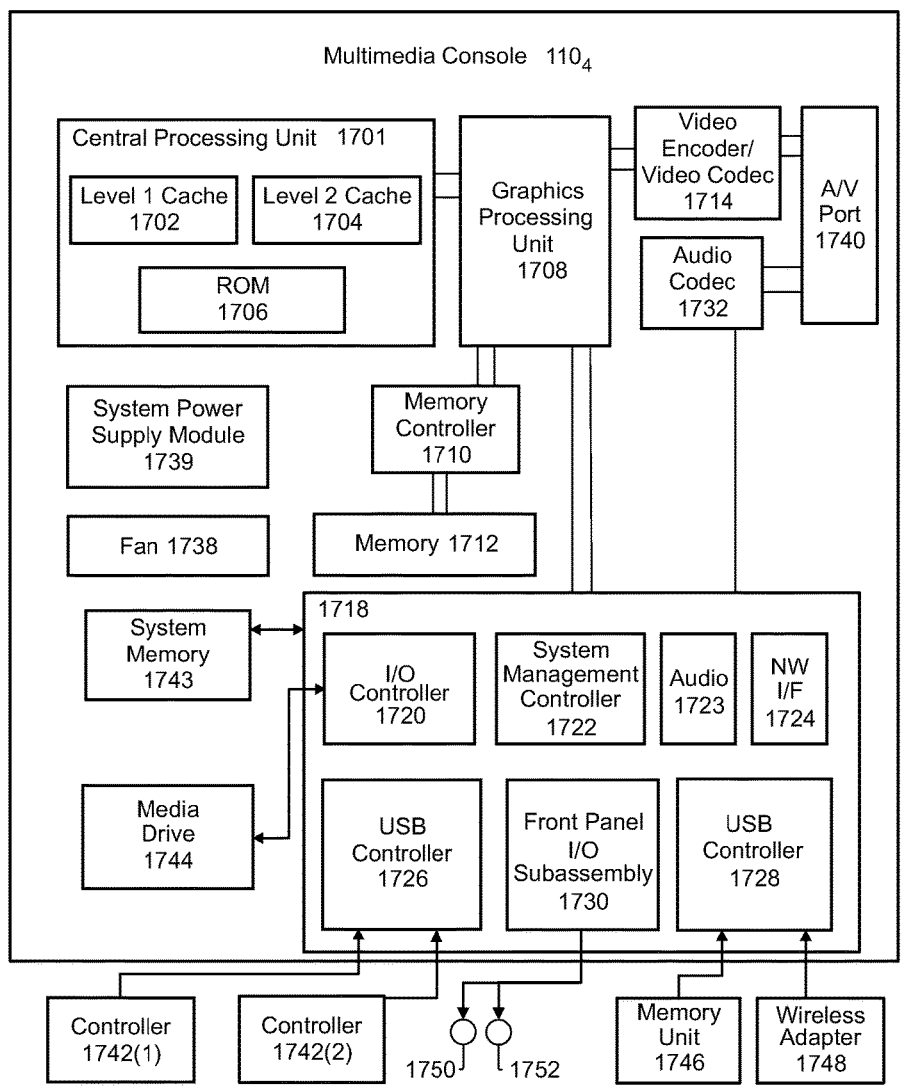
FIG. 17 is a block diagram of an illustrative multimedia console.

FIG. 17 is an illustrative functional block diagram of a multimedia console $110_4$. The multimedia console $110_4$ has a central processing unit (CPU) 1701 having a level 1 cache 1702, a level 2 cache 1704, and a Flash ROM (Read Only Memory) 1706. The level 1 cache 1702 and the level 2 cache 1704 temporarily store data and hence reduce the number of memory access cycles, thereby improving processing speed and throughput. The CPU 1701 may be configured with more than one core, and thus, additional level 1 and level 2 caches 1702 and 1704. The Flash ROM 1706 may store executable code that is loaded during an initial phase of a boot process when the multimedia console $110_4$ is powered ON.

A graphics processing unit (GPU) 1708 and a video encoder/video codec (coder/decoder) 1714 form a video processing pipeline for high speed and high resolution graphics processing. Data is carried from the GPU 1708 to the video encoder/video codec 1714 via a bus. The video processing pipeline outputs data to an A/V (audio/video) port 1740 for transmission to a television or other display. A memory controller 1710 is connected to the GPU 1708 to facilitate processor access to various types of memory 1712, such as, but not limited to, a RAM.

The multimedia console $110_4$ includes an I/O controller 1720, a system management controller 1722, an audio processing unit 1723, a network interface controller 1724, a first USB (Universal Serial Bus) host controller 1726, a second USB controller 1728, and a front panel I/O subassembly 1730 that are preferably implemented on a module 1718. The USB controllers 1726 and 1728 serve as hosts for peripheral controllers 1742(1) and 1742(2), a wireless adapter 1748, and an external memory device 1746 (e.g., Flash memory, external CD/DVD ROM drive, removable media). The network interface controller 1724 and/or wireless adapter 1748 provide access to a network (e.g., the Internet, home network) and may be any of a wide variety of various wired or wireless adapter components including an Ethernet card, a modem, a Bluetooth module, a cable modem, or the like.

System memory 1743 is provided to store application data that is loaded during the boot process. A media drive 1744 is provided and may comprise a DVD/CD drive, hard drive, or other removable media drive, etc. The media drive 1744 may be internal or external to the multimedia console $110_4$. Application data may be accessed via the media drive 1744 for execution, playback, etc. by the multimedia console $110_4$. The media drive 1744 is connected to the I/O controller 1720 via a bus, such as a Serial ATA bus or other high speed connection (e.g., IEEE 1394).

The system management controller 1722 provides a variety of service functions related to assuring availability of the multimedia console $110_4$. The audio processing unit 1723 and an audio codec 1732 form a corresponding audio processing pipeline with high fidelity and stereo processing. Audio data is carried between the audio processing unit 1723 and the audio codec 1732 via a communication link. The audio processing pipeline outputs data to the A/V port 1740 for reproduction by an external audio player or device having audio capabilities.

The front panel I/O subassembly 1730 supports the functionality of the power button 1750 and the eject button 1752, as well as any LEDs (light emitting diodes) or other indicators exposed on the outer surface of the multimedia console $110_4$. A system power supply module 1739 provides power to the components of the multimedia console $110_4$. A fan 1738 cools the circuitry within the multimedia console $110_4$.

The CPU 1701, GPU 1708, memory controller 1710, and various other components within the multimedia console $110_4$ are interconnected via one or more buses, including serial and parallel buses, a memory bus, a peripheral bus, and a processor or local bus using any of a variety of bus architectures. By way of example, such architectures can include a Peripheral Component Interconnects (PCI) bus and PCI-Express bus.

When the multimedia console $110_4$ is powered ON, application data may be loaded from the system memory 1743 into memory 1712 and/or caches 1702 and 1704 and executed on the CPU 1701. The application may present a graphical user interface that provides a consistent user experience when navigating to different media types available on the multimedia console $110_4$. In operation, applications and/or other media contained within the media drive 1744 may be launched or played from the media drive 1744 to provide additional functionalities to the multimedia console $110_4$.

The multimedia console $110_4$ may be operated as a standalone system by simply connecting the system to a television or other display. In this standalone mode, the multimedia console $110_4$ allows one or more users to interact with the system, watch movies, or listen to music. However, with the integration of broadband connectivity made available through the network interface controller 1724 or the wireless adapter 1748, the multimedia console $110_4$ may further be operated as a participant in a larger network community.

When the multimedia console $110_4$ is powered ON, a set amount of hardware resources are reserved for system use by the multimedia console operating system. These resources may include a reservation of memory (e.g., 16 MB), CPU and GPU cycles (e.g., 5%), networking bandwidth (e.g., 8 kbps), etc. Because these resources are reserved at system boot time, the reserved resources do not exist from the application's view.

In particular, the memory reservation preferably is large enough to contain the launch kernel, concurrent system applications, and drivers. The CPU reservation is preferably constant such that if the reserved CPU usage is not used by the system applications, an idle thread will consume any unused cycles.

With regard to the GPU reservation, lightweight messages generated by the system applications (e.g., pop-ups) are displayed by using a GPU interrupt to schedule code to render pop-ups into an overlay. The amount of memory needed for an overlay depends on the overlay area size and the overlay preferably scales with screen resolution. Where a full user interface is used by the concurrent system application, it is preferable to use a resolution independent of application resolution. A scaler may be used to set this resolution such that the need to change frequency and cause a TV re-sync is eliminated.

After the multimedia console $110_4$ boots and system resources are reserved, concurrent system applications execute to provide system functionalities. The system functionalities are encapsulated in a set of system applications that execute within the reserved system resources described above. The operating system kernel identifies threads that are system application threads versus gaming application threads. The system applications are preferably scheduled to run on the CPU 1701 at predetermined times and intervals in order to provide a consistent system resource view to the application. The scheduling is to minimize cache disruption for the gaming application running on the console.

When a concurrent system application requires audio, audio processing is scheduled asynchronously to the gaming application due to time sensitivity. A multimedia console application manager (described below) controls the gaming application audio level (e.g., mute, attenuate) when system applications are active.

Input devices (e.g., controllers 1742(1) and 1742(2)) are shared by gaming applications and system applications. The input devices are not reserved resources, but are to be switched between system applications and the gaming application such that each will have a focus of the device. The application manager preferably controls the switching of input stream, without knowledge of the gaming application's knowledge and a driver maintains state information regarding focus switches.

Various exemplary embodiments of the present optimized visibility for sleep sessions over time are now presented by way of illustration and not as an exhaustive list of all embodiments. An example includes a server device configured for controlling access to data from a remote client device over a network, comprising: one or more processors; a storage component arranged to receive read and write commands from the one or more processors; a network interface for supporting communications with the remote client device; and one or more memories storing computer-readable instructions which, when executed by the one or more processors, perform a method for controlling access to data from the remote client device comprising the steps of iteratively applying a graphing process to determine a number of sleep sessions that are expressible continuously on a sleep graph having a time axis and a calendar axis based on different beginning times for a range on a time axis, storing results from the graphing process for each of the different beginning times in the storage component, selecting a beginning time for the range from the stored results that provides a maximum number of continuously expressible sleep sessions, and controlling access by the remote client device to the sleep graph.

In another example, the server device further includes generating the sleep graph using the selected beginning time, the sleep graph expressing sleep sessions over a calendar period. In another example, the server device further includes exposing user controls to the remote device to enable one of selecting the calendar period or controlling one or more aspects of the generating. In another example, the generating is performed to centrally locate the sleep sessions in the sleep graph. In another example, the calendar period includes one of days, weeks, or months. In another example, the server device further includes configuring the sleep graph to include distributed sleep sessions and wrap one or more sleep sessions over boundaries in the calendar period. In another example, the server device further includes obtaining sleep data from a second remote client device, the second remote client device being configured as a companion to a wearable device having sensors to gather the sleep data. In another example, the server device further includes transforming the sleep data from the second remote client device to generate the sleep sessions. In another example, the server device further includes obtaining sleep session start and end times from the sleep data. In another example, the server device further includes exposing the sleep graph to a browser running on the remote client device.

A further example includes one or more computer-readable memories storing instructions which, when executed by one or more processors disposed in a computer server, control data received by a remote client device over a network, comprising: obtaining sleep data over a calendar period that describes sleep behaviors of a user from data obtained from one or more sensors; determining starting times and ending times for sleep sessions occurring over the calendar period from the sleep data; initiating a graphing process for a sleep graph having a time axis and a calendar axis by selecting an initial beginning time for a range of times expressed on the time axis; calculating a number of sleep sessions for which visibility is optimized on the sleep graph using a time range spanning the beginning time and a maximum end time for the sleep sessions; storing a result of the calculating in a storage component available to the server; incrementing the beginning time by an interval and repeating the calculating and storing until the calculating has been performed over a predetermined time period; adjusting the time axis to use a range having a beginning time that provides a maximum number of visibility optimized sleep sessions over the calendar period; and transmitting the sleep graph with the adjusted time axis to the remote client over the network.

In another example, the visibility is optimized using sleep sessions that are continuously expressed without breaks and the predetermined time period is 24 hours. In another example, the one or more computer-readable memories further include determining sleep quality using the sleep data. In another example, the one or more computer-readable memories further include configuring the sleep graph to express the sleep quality. In another example, the sleep quality includes one of light sleep, restful sleep, or wakefulness. In another example, the one or more computer-readable memories further include adjusting the calendar axis on the sleep graph to capture one or more additional sleep sessions.

A further example includes a method for optimizing visibility of sleep sessions over a calendar period on a device, the method comprising the steps of: communicating with a wearable device that is configured for collecting biometric data from a wearable device user, transforming the collected biometric data into sleep data describing sleep behaviors of the user; and rendering a sleep graph on a user interface of the device, the rendered sleep graph being configured to optimize visibility of sleep sessions derived, at least in part, from the sleep data, the optimization including rendering a majority of the sleep sessions in a continuous, non-broken manner in the sleep graph.

In another example, the optimization is implemented using an automated graphing process and further includes substantially locating a majority of the sleep sessions in a central portion of the sleep graph. In another example, the method further includes transmitting the sleep data to a remote service over a network. In another example, the method further includes one of generating the sleep graph locally on the device or receiving the sleep graph from the remote service over the network.

Based on the foregoing, it may be appreciated that technologies for implementing optimized visibility for sleep sessions over time have been disclosed herein. Although the subject matter presented herein has been described in language specific to computer structural features, methodological and transformative acts, specific computing machinery, and computer-readable storage media, it is to be understood that the invention defined in the appended claims is not necessarily limited to the specific features, acts, or media described herein. Rather, the specific features, acts, and mediums are disclosed as example forms of implementing the claims.

The subject matter described above is provided by way of illustration only and may not be construed as limiting. Various modifications and changes may be made to the subject matter described herein without following the example embodiments and applications illustrated and described, and without departing from the true spirit and scope of the present invention, which is set forth in the following claims.

What is claimed:

1. A server device configured for controlling access to data from a remote client device over a network, comprising:
one or more processors;

a storage component arranged to receive read and write commands from the one or more processors;

a network interface for supporting communications with the remote client device; and one or more memories storing computer-readable instructions which, when executed by the one or more processors, perform a method for controlling access to data from the remote client device comprising the steps of iteratively applying a graphing process to determine a number of sleep sessions that are expressible continuously on a sleep graph having a time axis and a calendar axis based on different beginning times for a range of multiple days on the time axis, wherein the graphing process is configured to:

identify a number of continuously expressible sleep sessions with different beginning times applied to each of the multiple days, each identified number is associated with a single constant beginning time for each of the days; and calculate a total number of continuously expressible sleep sessions for each constant beginning time for each day;

storing results from the graphing process for each of the different beginning times in the storage component, selecting the constant beginning time for the range of multiple days from the stored results using the calculated total numbers that provides a maximum number of continuously expressible sleep sessions, the continuously expressible sleep sessions depict a representation of each sleep session along a single representation of a respective row or column, in which the selection causes an adjustment to the continuously expressible sleep sessions from being non-continuously displayed to being continuously displayed, and controlling access by the remote client device to the sleep graph.

2. The server device of claim 1 further including generating the sleep graph using the selected beginning time, the sleep graph expressing sleep sessions over a calendar period.

3. The server device of claim 2 further including exposing user controls to the remote device to enable one of selecting the calendar period or controlling one or more aspects of the generating.

4. The server device of claim 2 in which the generating is performed to centrally locate the sleep sessions in the sleep graph.

5. The server device of claim 2 in which the calendar period includes one of days, weeks, or months.

6. The server device of claim 1 further including configuring the sleep graph to include distributed sleep sessions and wrap one or more sleep sessions over boundaries in the calendar period.

7. The server device of claim 1 further including obtaining sleep data from a second remote client device, the second remote client device being configured as a companion to a wearable device having sensors to gather the sleep data.

8. The server device of claim 7 further including transforming the sleep data from the second remote client device to generate the sleep sessions.

9. The server device of claim 8 further including obtaining sleep session start and end times from the sleep data.

10. The server device of claim 1 further including exposing the sleep graph to a browser running on the remote client device.

11. One or more computer-readable memories storing instructions which, when executed by one or more processors disposed in a computer server, control data received by a remote client device over a network, comprising:

obtaining sleep data over a calendar period that describes sleep behaviors of a user from data obtained from one or more sensors;

determining starting times and ending times for sleep sessions occurring over the calendar period from the sleep data;

initiating a graphing process for a sleep graph having a time axis and calendar axis by selecting an initial beginning time for a range of times expressed on the time axis;

calculating a number of sleep sessions for which visibility is optimized on the sleep graph using a time range spanning the beginning time and a maximum end time for the sleep sessions;

storing a result of the calculating in a storage component available to the server;

incrementing the beginning time by an interval and repeating the calculating and storing until the calculating has been performed over a predetermined time period;

adjusting the time axis to use a range having a beginning time that provides a maximum number of visibility optimized sleep sessions over the calendar period, the maximum number of visibility optimized sleep sessions depicts a representation of each sleep session along a single representation of a respective row or column, in which the adjusting changes the continuously expressible sleep sessions from being non-continuously displayed to being continuously displayed; and transmitting the sleep graph with the adjusted time axis to the remote client over the network.

12. The one or more computer-readable memories of claim 11 in which visibility is optimized using sleep sessions that are continuously expressed without breaks and the predetermined time period is 24 hours.

13. The one or more computer-readable memories of claim 11 further including determining sleep quality using the sleep data.

14. The one or more computer-readable memories of claim 13 further including configuring the sleep graph to express the sleep quality.

15. The one or more computer-readable memories of claim 14 in which the sleep quality includes one of light sleep, restful sleep, or wakefulness.

16. The one or more computer-readable memories of claim 11 further including adjusting the calendar axis on the sleep graph to capture one or more additional sleep sessions.

17. A method for optimizing visibility of sleep sessions over a calendar period on a device, the method comprising the steps of:

communicating with a wearable device that is configured for collecting biometric data from a wearable device user;

transforming the collected biometric data into sleep data describing sleep behaviors of the user;

identifying a number of continuously expressible sleep sessions with different beginning times applied to multiple days, each identified number is associated with a single constant beginning time for each of the multiple days;

calculating a total number of continuously expressible sleep sessions for each constant beginning time for each day; and rendering a sleep graph on a user interface of the device, the rendered sleep graph being configured to optimize visibility in the form of continuously expressible sleep sessions derived, at least in part, from the calculated total number of continuously expressible sleep sessions for each constant beginning time, the continuously expressible sleep sessions including transforming sleep sessions from being non-continuously rendered along multiple rows or columns in the sleep graph to being rendered in a continuous, non-broken manner in the sleep graph.

18. The method of claim 17 in which the optimization is implemented using an automated graphing process and further includes substantially locating a majority of the sleep sessions in a central portion of the sleep graph.

19. The method of claim 17 further including transmitting the sleep data to a remote service over a network.

20. The method of claim 19 further including one of generating the sleep graph locally on the device or receiving the sleep graph from the remote service over the network.

* * * * *